US012653946B2

(12) United States Patent
Cook et al.

(10) Patent No.: US 12,653,946 B2
(45) Date of Patent: Jun. 16, 2026

(54) USER-WEARABLE INFUSION PUMP HOLDER

(71) Applicant: Tandem Diabetes Care, Inc., San Diego, CA (US)

(72) Inventors: Steven B. Cook, Oceanside, CA (US); Philip Sven Lamb, San Diego, CA (US); Ryan William Betts, San Diego, CA (US); Michael Michaud, San Diego, CA (US); Virginia Lu, San Diego, CA (US); Neel Shah, San Diego, CA (US); Jacob Pearlman, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 769 days.

(21) Appl. No.: 18/075,029

(22) Filed: Dec. 5, 2022

(65) Prior Publication Data

US 2023/0173170 A1     Jun. 8, 2023

Related U.S. Application Data

(60) Provisional application No. 63/347,894, filed on Jun. 1, 2022, provisional application No. 63/332,974, filed on Apr. 20, 2022, provisional application No. 63/285,794, filed on Dec. 3, 2021.

(51) Int. Cl.
A61M 5/142          (2006.01)
(52) U.S. Cl.
CPC .............................. A61M 5/14248 (2013.01)

(58) Field of Classification Search
CPC .......... A61M 5/14244; A61M 5/14248; A61M 5/1413; Y10S 224/93; A45C 11/022; A45C 5/02
See application file for complete search history.

(56) References Cited

U.S. PATENT DOCUMENTS

| | | |
|---|---|---|
| 3,451,422 A | 6/1969 | Chorkey |
| 3,833,030 A | 9/1974 | Waldbauer, Jr. et al. |
| 3,860,353 A | 1/1975 | Lukasik et al. |
| 4,718,893 A | 1/1988 | Dorman et al. |
| 4,908,017 A | 3/1990 | Howson et al. |
| 5,080,653 A | 1/1992 | Voss et al. |
| 5,097,122 A | 3/1992 | Colman et al. |
| | (Continued) | |

FOREIGN PATENT DOCUMENTS

| | | | |
|---|---|---|---|
| CA | 2038840 C | 11/1994 | |
| EP | 3915611 A1 * | 12/2021 | ........ A61M 5/14248 |
| | (Continued) | | |

OTHER PUBLICATIONS

International Search Report and Written Opinion for Application No. PCT/US2022/051838 mailed Apr. 24, 2023.
(Continued)

*Primary Examiner* — Laura A Bouchelle
(74) *Attorney, Agent, or Firm* — Merchant & Gould P.C.

(57)          ABSTRACT
Embodiments of the present disclosure relate to a holder or carrier for a user-wearable infusion pump that can be worn on or near the patient's body. Embodiments depicted and described herein provide a more versatile and secure way to hold and carry a user-wearable infusion pump.

13 Claims, 36 Drawing Sheets

(56)                    References Cited

U.S. PATENT DOCUMENTS

| | | | |
|---|---|---|---|
| 5,167,633 | A | 12/1992 | Mann et al. |
| 5,186,805 | A | 2/1993 | Gross et al. |
| 5,256,157 | A | 10/1993 | Samiotes et al. |
| 5,370,622 | A | 12/1994 | Livingston et al. |
| 5,376,070 | A | 12/1994 | Purvis et al. |
| 5,395,320 | A | 3/1995 | Padda et al. |
| 5,462,525 | A | 10/1995 | Srisathapat et al. |
| 5,466,218 | A | 11/1995 | Srisathapat et al. |
| 5,505,709 | A | 4/1996 | Funderburk et al. |
| 5,514,103 | A | 5/1996 | Srisathapat et al. |
| 5,647,853 | A | 7/1997 | Feldmann et al. |
| 5,665,065 | A | 9/1997 | Colman et al. |
| 5,785,681 | A | 7/1998 | Indravudh |
| 5,957,890 | A | 9/1999 | Mann et al. |
| 5,961,305 | A | 10/1999 | Eek et al. |
| 6,006,798 | A | 12/1999 | Lindquist |
| 6,122,536 | A | 9/2000 | Sun et al. |
| 6,176,401 | B1 | 1/2001 | Lim |
| 6,283,943 | B1 | 9/2001 | Dy et al. |
| 6,362,591 | B1 | 3/2002 | Moberg |
| 6,461,331 | B1 | 10/2002 | Van Antwerp |
| D467,068 | S | 12/2002 | Lewis et al. |
| D534,720 | S | 1/2007 | Infanti et al. |
| 7,471,994 | B2 | 12/2008 | Ford et al. |
| D594,226 | S | 6/2009 | Hofer et al. |
| 7,630,745 | B2 | 12/2009 | Chen et al. |
| 7,753,713 | B2 | 7/2010 | Neale, III |
| 7,931,642 | B2 | 4/2011 | Tonnies |
| 7,967,773 | B2 | 6/2011 | Amborn et al. |
| 7,967,785 | B2 | 6/2011 | Morgan et al. |
| D644,428 | S | 9/2011 | Feng |
| 8,105,351 | B2 | 1/2012 | Lehman et al. |
| 8,172,798 | B2 | 5/2012 | Hungerford et al. |
| 8,277,435 | B2 | 10/2012 | Estes |
| 8,282,626 | B2 | 10/2012 | Wenger et al. |
| 8,475,409 | B2 | 7/2013 | Tsoukalis |
| 8,568,361 | B2 | 10/2013 | Yodfat et al. |
| 8,573,027 | B2 | 11/2013 | Rosinko et al. |
| 8,882,701 | B2 | 11/2014 | DeBelser et al. |
| 9,213,903 | B1 | 12/2015 | Laska et al. |
| 9,662,440 | B2 | 5/2017 | Yodfat et al. |
| 9,731,072 | B2 | 8/2017 | Estes |
| 9,744,290 | B2 | 8/2017 | Tieck et al. |
| 9,764,087 | B2 | 9/2017 | Peterfreund et al. |
| 10,279,106 | B1 | 5/2019 | Cook |
| 10,279,107 | B2 | 5/2019 | Michaud |
| 10,525,211 | B2 | 1/2020 | Geipel et al. |
| 10,632,257 | B2 | 4/2020 | Estes et al. |
| 11,596,731 | B2 | 3/2023 | Saint |
| 2005/0277887 | A1 | 12/2005 | Douglas et al. |
| 2006/0084924 | A1 | 4/2006 | Koch |
| 2006/0293577 | A1 | 12/2006 | Morrison et al. |
| 2010/0114027 | A1 | 5/2010 | Jacobson et al. |
| 2011/0054400 | A1 | 3/2011 | Chong et al. |
| 2011/0264043 | A1 | 10/2011 | Kotnik et al. |
| 2012/0078185 | A1 | 3/2012 | Smith et al. |
| 2012/0160723 | A1 | 6/2012 | Harms et al. |
| 2013/0053816 | A1 | 2/2013 | Diperna et al. |
| 2013/0191770 | A1 | 7/2013 | Bartz et al. |
| 2016/0339172 | A1 | 11/2016 | Michaud et al. |
| 2019/0351134 | A1 | 11/2019 | Cook et al. |
| 2020/0384197 | A1 | 12/2020 | Chiu et al. |

FOREIGN PATENT DOCUMENTS

| | | |
|---|---|---|
| WO | 2007/079016 A2 | 7/2007 |
| WO | 2016/176251 A1 | 11/2016 |

OTHER PUBLICATIONS

European Search Report of the European Patent Office, EP No. 22902285.0, mailed Oct. 28, 2025, 13 pages.

* cited by examiner

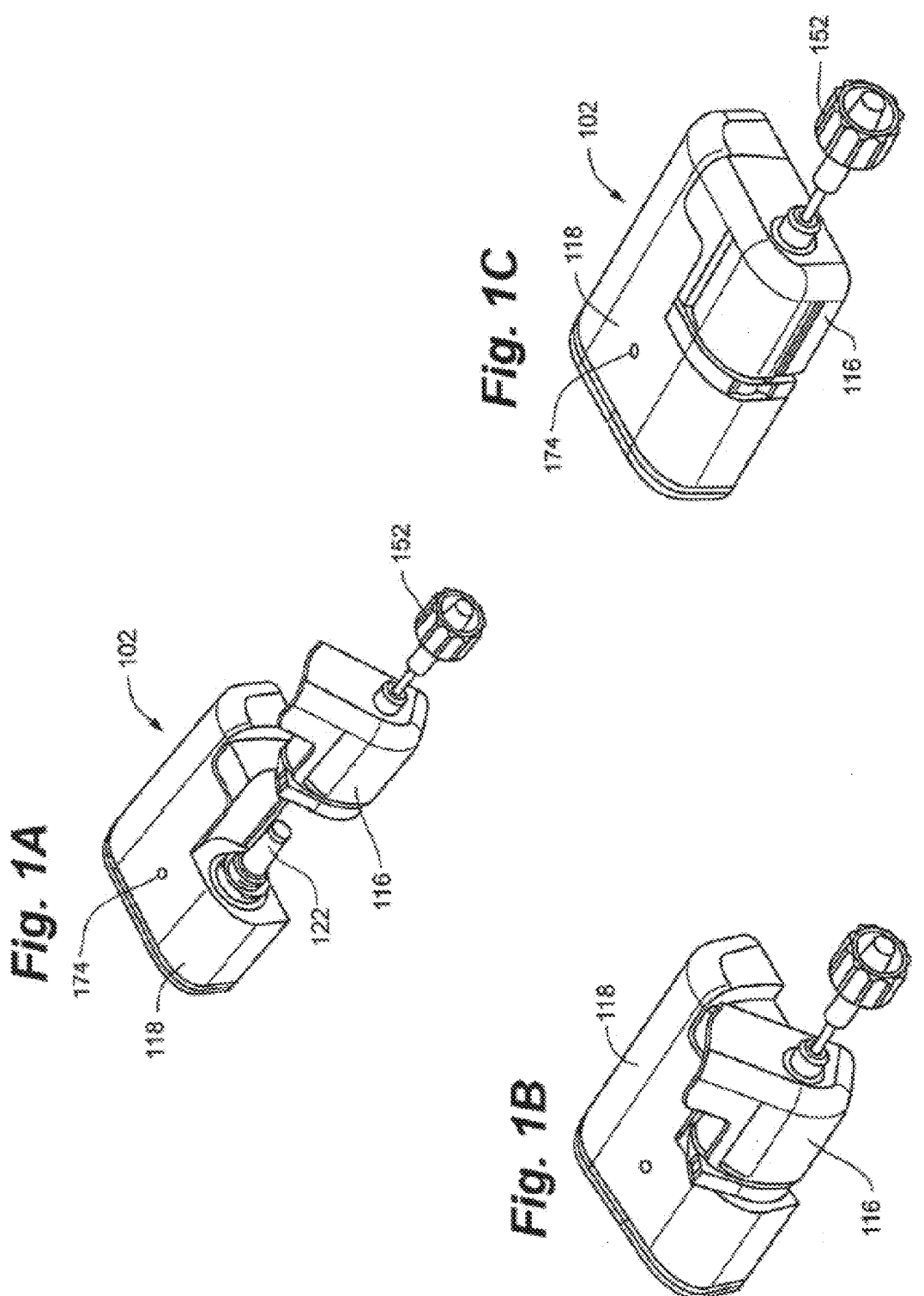

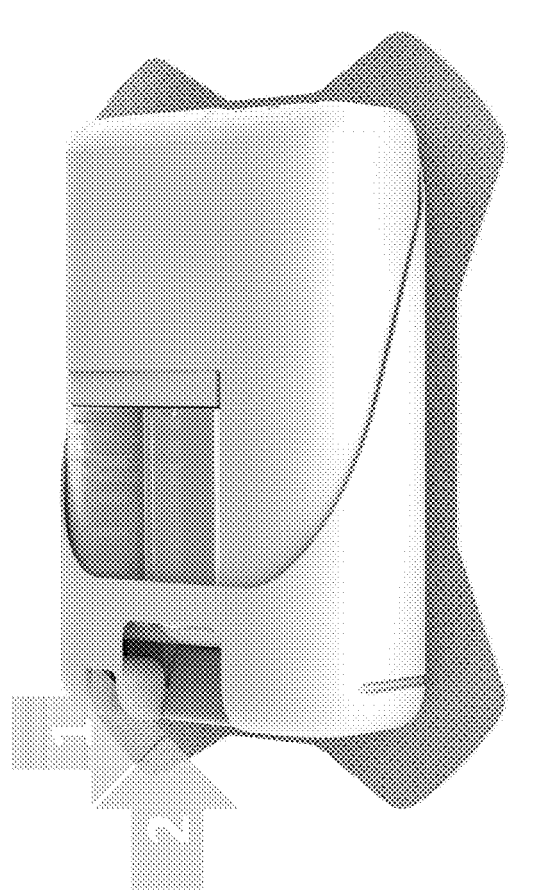
*Fig. 22G*
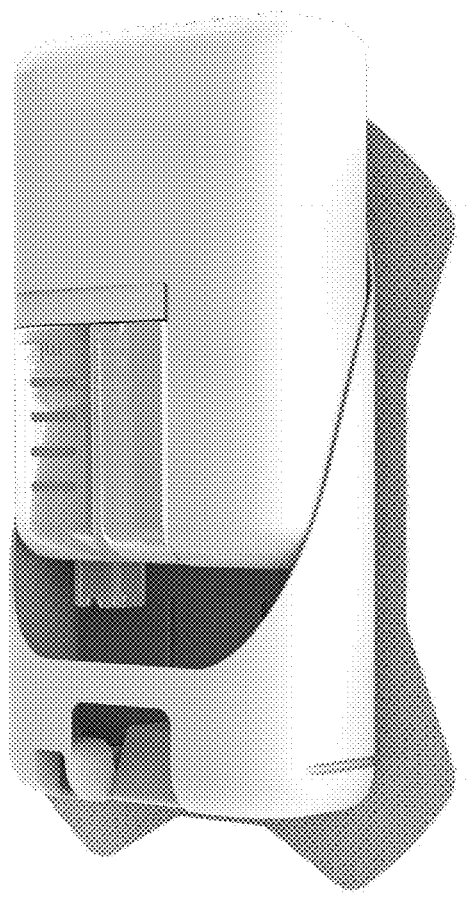
*Fig. 22H*

USER-WEARABLE INFUSION PUMP HOLDER

RELATED APPLICATION

The present application claims the benefit of U.S. Provisional Application No. 63/285,794, filed Dec. 3, 2021, and of U.S. Provisional Application No. 63/332,974, filed Apr. 20, 2022, and of U.S. Provisional Application No. 63/347,894, filed Jun. 1, 2022, each of which is hereby incorporated herein in its entirety by reference.

TECHNICAL FIELD

The present disclosure relates to medical pumps for delivering medicament to a patient, and more specifically, to a user-wearable infusion pump that can be worn on the body of a user.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

One type of pump that has been developed is a patch pump also known as a micro pump. Patch pumps are small pumps, typically ambulatory, that may be carried directly on the skin under the user's clothing. In some cases, the pumps are situated directly on, or very near to, the injection site such that little or no tubing is required to deliver the insulin or other medicament to the patient. These pumps can therefore be worn directly on the body of the user or carried in close proximity to the body. Typically, patch pumps that are worn on the body are affixed to the body with an adhesive patch. Some patch pumps include a single button on the pump to initiate delivery of medicament and do not include a built-in display or user interface. These pumps are therefore primarily remote-controlled, which enables programming of the devices without removing them from the body.

SUMMARY

Embodiments of the present disclosure relate to a holder or carrier for a user-wearable infusion pump that can be worn on or near the patient's body. Embodiments depicted and described herein provide a more versatile and secure way to hold and carry a user-wearable infusion pump.

In an embodiment, a user-wearable infusion pump system can include a user-wearable infusion pump configured to contain a medicament having a flexible clip disposed on a perimeter of the user-wearable infusion pump. The system can further include a pump holder configured to releasably hold the user-wearable infusion pump and having an adhesive patch configured to retain the pump holder on a body of a user. The pump holder can include a frame base and a perimeter wall extending around the frame base having a shape matching the perimeter of the user-wearable infusion pump. The pump holder can further include a slot configured to selectively receive the flexible clip of the user-wearable infusion pump that provides a snap fit with the flexible clip to releasably retain the user-wearable infusion pump on the pump holder.

In an embodiment, a pump holder for a user-wearable infusion pump can include an adhesive patch configured to retain the pump holder on a body of a user, a frame base and a perimeter wall extending around the frame base having a shape matching a perimeter of a user-wearable infusion pump. The pump holder can further include a slot configured to selectively receive a flexible clip of the user-wearable infusion pump that provides a snap fit with the flexible clip to releasably retain the user-wearable infusion pump on the pump holder.

In an embodiment, a user-wearable infusion configured to contain a medicament includes a flexible clip disposed on a perimeter of the user-wearable infusion pump. The flexible clip of the user-wearable infusion pump can be configured to provide a snap fit with a slot on a pump holder to releasably retain the user-wearable infusion pump on the pump holder.

In an embodiment, a user-wearable infusion pump system includes a user-wearable infusion pump configured to contain a medicament, the user-wearable infusion pump including a flexible clip disposed on a perimeter of the user-wearable infusion pump and a retention slot formed in a body of the pump on an opposite end of the pump from the flexible clip. A pump holder can be configured to releasably hold the user-wearable infusion pump and include an adhesive patch configured to retain the pump holder on a body of a user. The pump holder can include a frame base and a perimeter wall extending at least partially around the frame base having a shape matching the perimeter of the user-wearable infusion pump. A projection can extend inwardly from the perimeter wall and be configured to interface with the retention slot of the pump. A slot can be configured to selectively receive the flexible clip of the user-wearable infusion pump and provide a snap fit with the flexible clip to releasably retain the user-wearable infusion pump on the pump holder.

In an embodiment, a pump holder for a user-wearable infusion pump can include an adhesive patch configured to retain the pump holder on a body of a use, a frame base and a perimeter wall extending at least partially around the frame base having a shape matching a perimeter of a user-wearable infusion pump. A projection can extend inwardly from the perimeter wall and be configured to interface with a retention slot of the pump. A slot can be configured to selectively receive a flexible clip of the user-wearable infusion pump and to provide a snap fit with the flexible clip to releasably retain the user-wearable infusion pump on the pump holder.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1C depicts an embodiment of a pump system according to the disclosure.

FIGS. 22A-22H depict an embodiment of a pump system according to the disclosure.

Figures 2A, 2B:
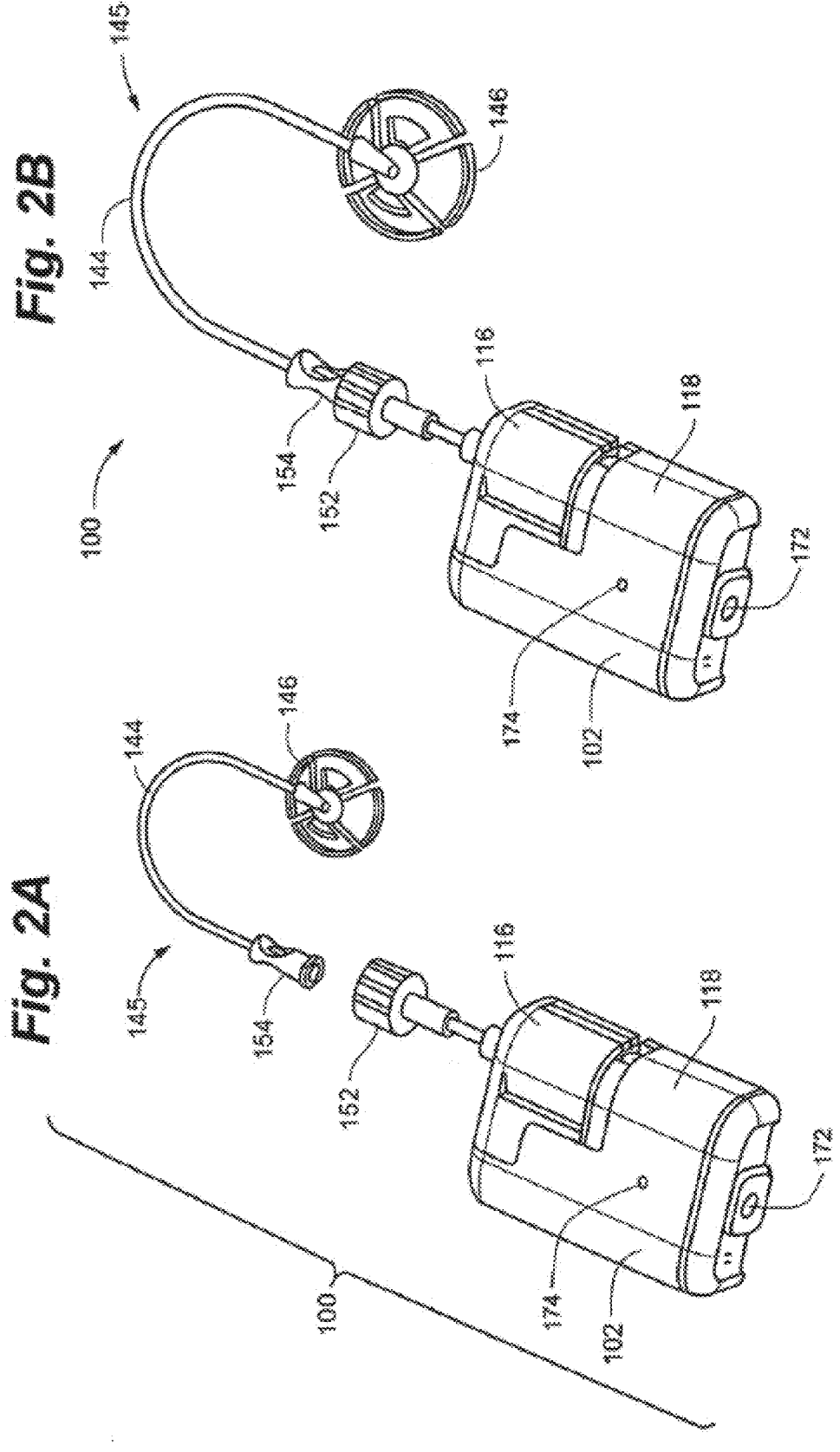
FIGS. 2A-2B depict an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIGS. 1A-1C, a pump system 100 including a pump 102 is depicted in accordance with an embodiment of the disclosure. Drive unit 118 of pump 102 includes a drive mechanism 122 that mates with a recess in medicament cartridge 116 of pump 102 to attach the medicament cartridge 116 to the drive unit 118. Further details regarding example embodiments of such delivery mechanisms can be found in U.S. Patent Publication No. 2017/0049957, which is hereby incorporated by reference in its entirety. In some embodiments, cartridge 116 can rotationally attach to drive unit 118 as shown in FIGS. 1B-1C. Further details regarding such rotational attachment can be found in, for example, U.S. Pat. No. 9,993,595, which is hereby incorporated by reference in its entirety.

As depicted in the embodiment of FIGS. 2A-2B, pump system 100 can include a pump 102 and an infusion set 145. FIG. 2A depicts this infusion set 145 as not connected to pump while FIG. 2B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user, while pump 102 can be carried in a separate location, such as the user's pocket or another location on the user's body. Various lengths of tubing 144 can be used in this embodiment to accommodate the user's preference. Further details regarding such pumps can be found in U.S. Pat. Nos. 9,993,595; 10,279,106; and 10,279,107, each of which is hereby incorporated herein by reference in its entirety.

In one embodiment, pump 102 includes a processor that controls operations of the pump and, in some embodiments, may communicate in either one-way or two-way modes to, e.g., receive operational commands and/or other signals, including data, from a separate device and/or, e.g., to send signals, including data, to a separate device. Pump 102 can include one or more buttons configured to cause the processor to initiate one or more functions. In the depicted embodiment, pump 102 includes only a single button 172, although more than one button may be present on pump 102. Button 172 can be configured to, for example, initiate delivery of medicament. Any single button such as button 172 can be utilized to execute a plurality of functions or operations. For example, a single press of button may initiate one function, holding the button down for a predetermined period of time may initiate another function, etc. Because the depicted pump 102 optionally does not itself include a display or user interface, information and feedback regarding medicament delivery or dosing initiated with button 172 can be communicated to and displayed on a remote control device or other device having a display and/or other type of user interface. Further details regarding use of button 172 can be found in U.S. Patent Publication No. 2018/0193555, which is hereby incorporated by reference in its entirety and is attached hereto as Appendix A.

In one embodiment, pump 102 includes a light source, such as a light emitting diode (LED) 174. Light source 174 can be configured to provide user feedback regarding user input and/or the performance of a desired function. For example, in one embodiment, light source 174 can illuminate or blink one or more times to indicate that the one or more buttons 172 have been activated and/or that a desired function has been initiated. In one embodiment, pump 102 can additionally and/or alternatively vibrate and/or provide audible notifications to indicate that the one or more buttons 172 have been activated and/or that a desired function has been initiated or, e.g., to provide user feedback regarding user input and/or the performance of the desired function. Illumination of light source 174 and/or vibrations and/or audible notifications may be executed in any number of patterns, frequencies, durations, sequences, combinations, colors, brightness levels, etc. to indicate particular information, such as particular input received and/or particular functions or operations enabled and/or initiated, to the pump user or caregiver. In some embodiments pump can include two or more indicator lights 174.

Figures 3A, 3B, 3C:
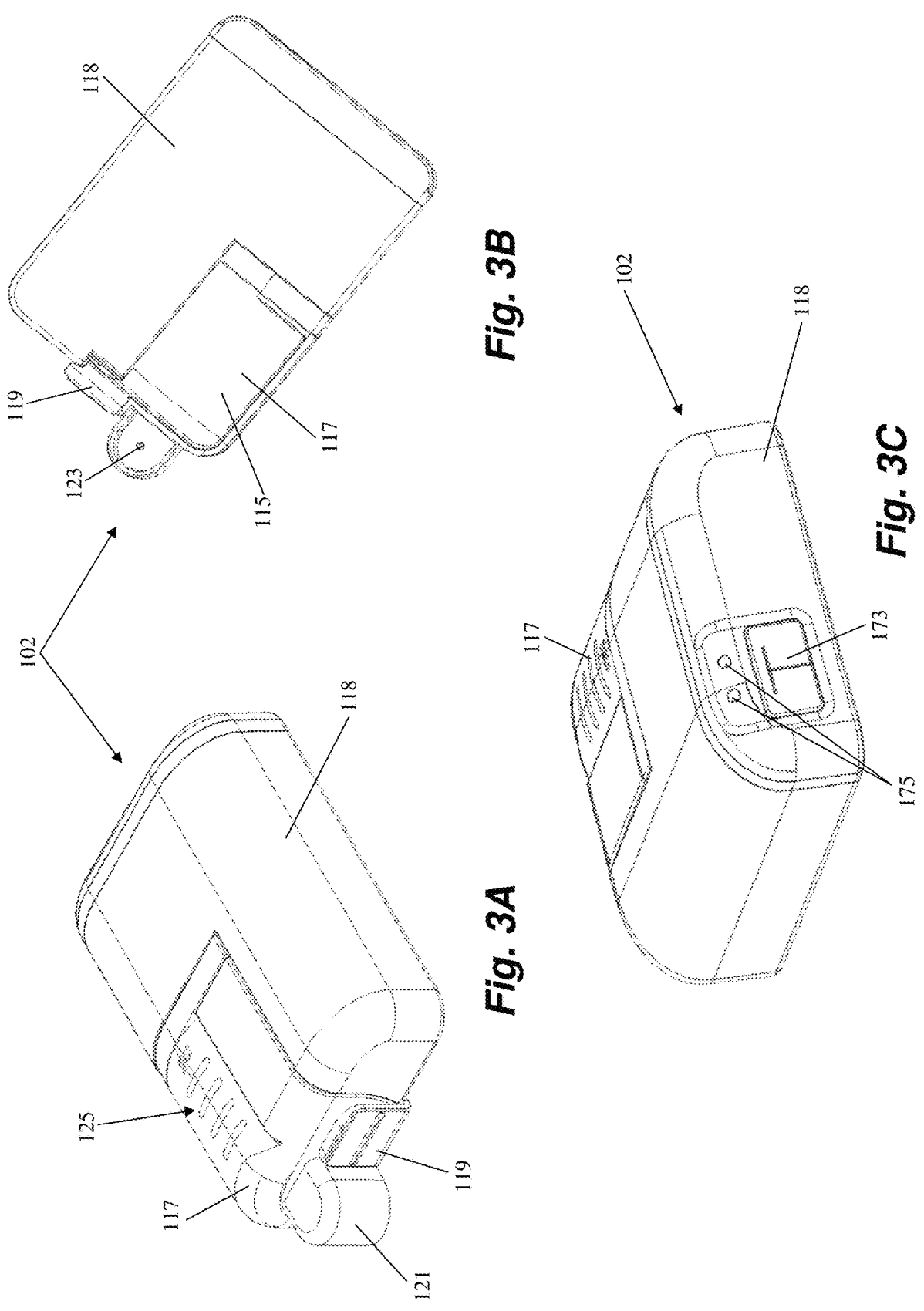
FIGS. 3A-3C depict an embodiment of a pump system according to the disclosure.

As noted above, in some embodiments pump 102 can be provided with a connector 152 extending from tubing attached to the pump 102 to an infusion set 145 for delivery of medicament at a site displaced from the pump 102. In other embodiments, pump 102 can be configured to deliver medicament through a cannula extending directly beneath the pump 102. One example of a pump 102 capable of delivering medicament from a cartridge 117 in this manner is depicted in FIGS. 3A-3C. In some embodiments, a common drive unit 118 can be used interchangeably with a cartridge 116 having tubing and a connector 152 for use with an infusion set 152 and a cartridge 117 configured to deliver medicament through a cannula directly below the cartridge 117 to meet the needs of the user at a given time.

Referring now to FIGS. 3A-3C, a user-wearable infusion pump 102 including a cartridge 117 capable of delivering medicament through a cannula directly beneath the pump is depicted. Cartridge 117 can, in some embodiments, rotationally attach to a drive unit 118 that includes an input button 173 and a pair of indicator lights 175. Cartridge 117 can be at least partially comprised of a transparent material and include graduated markings 125 to enable a user to visually determine am amount of medicament in the cartridge reservoir 115. Cartridge can further include a cannula interface 121 having an outlet 123 fluidly connected to the interior of the reservoir 115 and configured to interface with a cannula extending below the pump to deliver medicament from the reservoir 115 to the user. A clip 119 can be disposed on cartridge 117 to enable the pump 102 to be attached to and detached from a pump holder, as will be described in more detail below. In some embodiments, cartridge 117 is configured to be refilled while in other embodiments the cartridge 117 is disposable and discarded after a single use to be replaced with a new cartridge. If the cartridge is disposable, one advantage of providing the clip 119 on the cartridge is that if the clip is broken or otherwise damaged a new cartridge can be attached to the re-usable drive unit 118 with a functioning clip 119.

Figures 4A, 4B:
FIGS. 4A-4B depict an embodiment of a drive unit for the pump system of FIGS. 3A-3C.
Figures 5A, 5B:
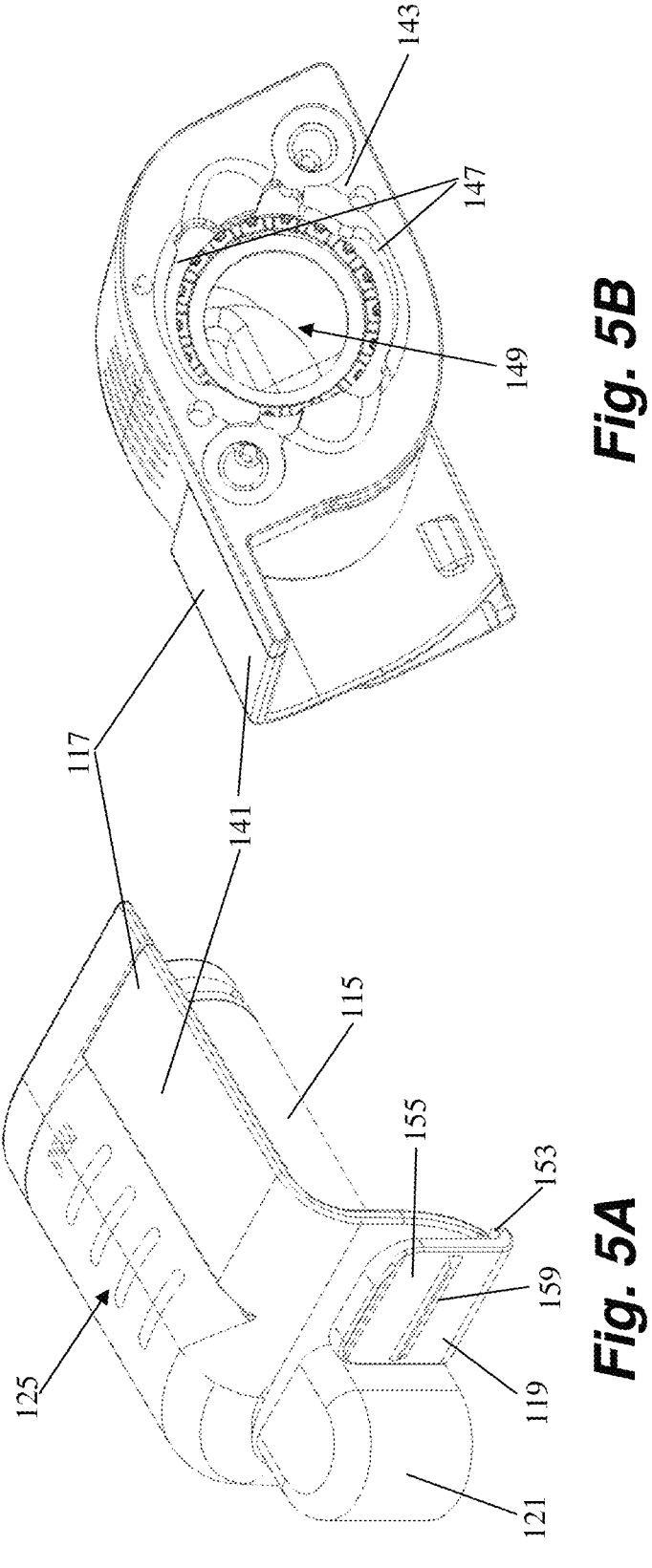
FIGS. 5A-5D depict an embodiment of a cartridge for the pump system of FIGS. 3A-3C.
Figure 5D:
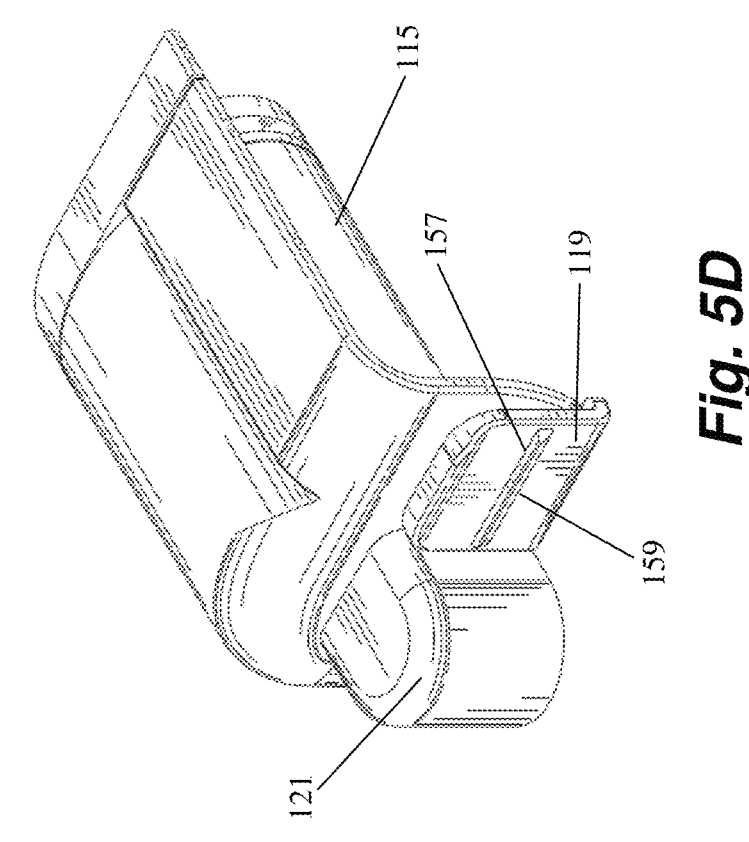
Figure 5C:
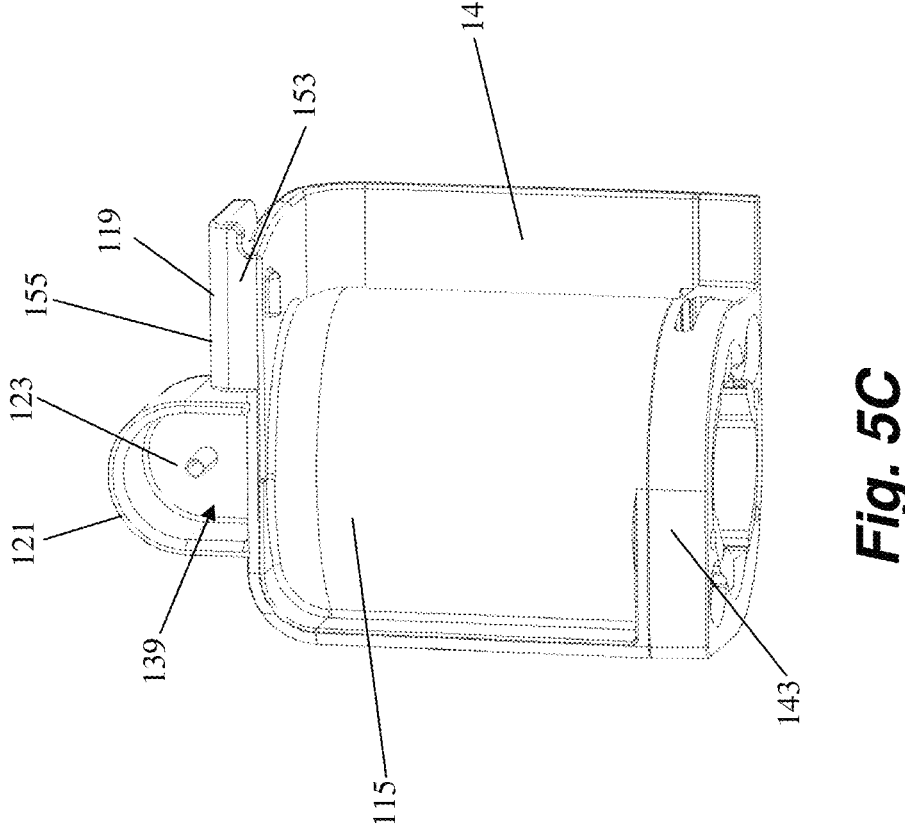

Further details regarding drive unit 118 of the pump 102 of FIGS. 3A-3C are depicted in FIGS. 4A-4B. Drive unit can include a cartridge attachment projection 133 configured to receive an opening in the cartridge 117 for rotational attachment of the cartridge 117 to the drive unit 118. Cartridge attachment 133 can include locking flanges 135 that interlock with corresponding features of the cartridge 117 when the cartridge is rotated about cartridge attachment 133. An aperture 137 can also be formed through cartridge attachment 133 extending into drive unit 118. In operation, a drive screw can extend from drive unit 118 and project out of aperture 137 and into cartridge 117 with a plunger disposed within reservoir 115 of cartridge 117 such that advancement of the lead screw by the drive unit 118 causes the plunger to advance within the reservoir 115 to incrementally dispense medicament from the reservoir 115. Drive unit 118 can also include an offset 127 defining recessed surfaces 129 and a curved inset surface 131 that interface with corresponding features of the cartridge 117 when rotated into engagement with the drive unit 118 as discussed in more detail below.

Referring now to FIGS. 5A-5D, further details regarding cartridge 117 are depicted. As noted above, cartridge 117 includes a medicament reservoir 115 and a cannula interface 121 having an open interior 139 and an outlet 124 projecting into the open interior 139 for interfacing with a cannula to deliver medicament from the reservoir. As will be discussed in more detail below, cartridge 117 can further include clip 119 that aids in attaching the pump to and detaching the pump from a pump holder. Clip can generally include an elongate tab 155 connected to the cartridge 117 with a unitarily formed connector portion 153 that enables the elongate tab 155 to flex inwardly and outwardly with respect to the cartridge 117. The clip 119 can include an outwardly projecting locking projection 159 on the elongate tab 155 have an upwardly facing planar locking surface 157. To attach the cartridge 117 to the drive unit 118, cartridge opening 149 of cartridge 117 can be inserted onto the drive unit 118 and the cartridge 117 rotated to interlock the locking flanges 135 on the cartridge attachment 133 of the drive unit 118 with corresponding locking recesses 147 on the pump attachment feature 143 disposed at the end of the cartridge 117. As the cartridge 117 is rotated, an outer curved surface of reservoir 115 slides into curved insert surface 131 of offset 127 of drive unit 118 and a flange 141 projecting outwardly from reservoir 115 contacts recessed surfaces 129 of offset 127 to align the outer surfaces of cartridge 117 parallel and flush with the outer surfaces of drive unit 118 and to prevent over rotation of cartridge 117 relative to drive unit 118.

Figures 6A, 6B:
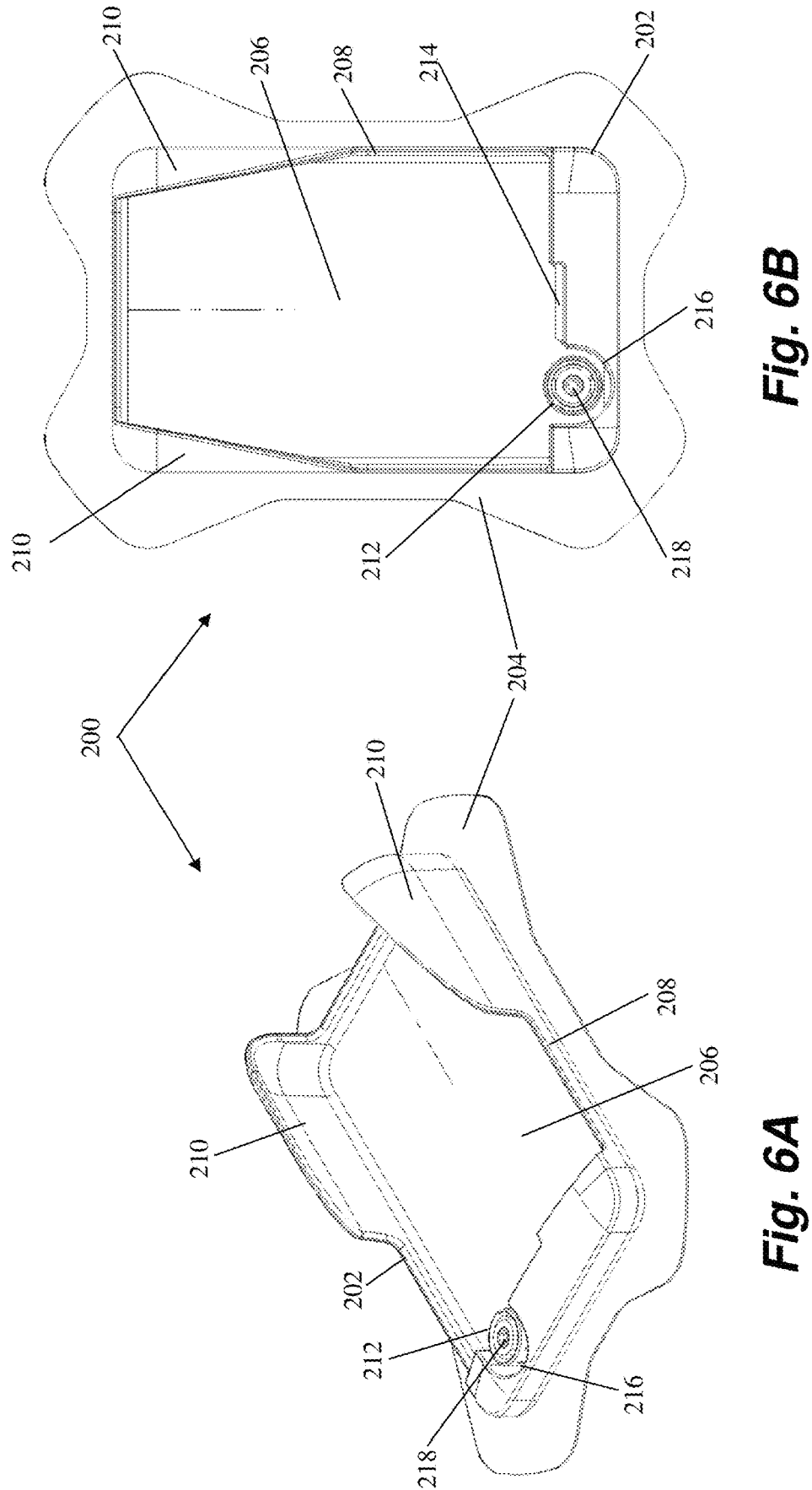
FIGS. 6A-6D depict an embodiment of a holder for a user-wearable infusion pump according to an embodiment of the disclosure.
Figure 6C:
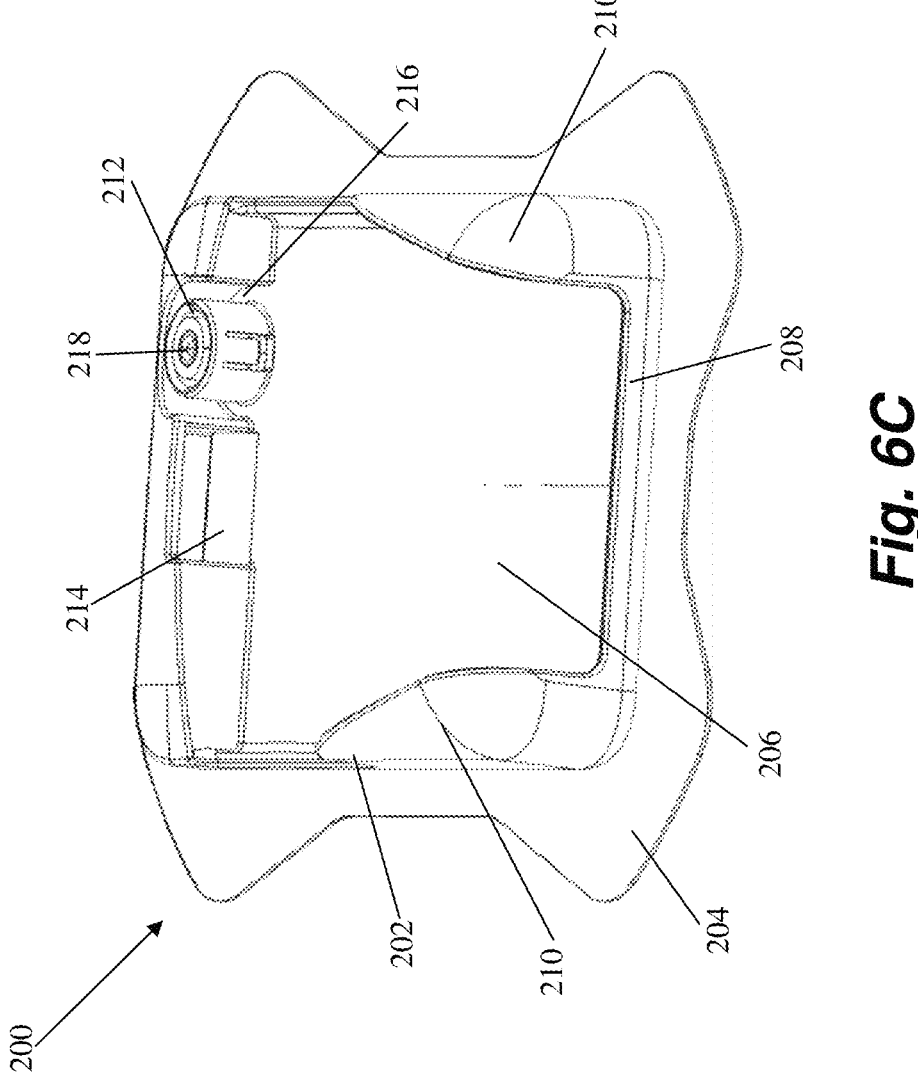
Figure 6D:
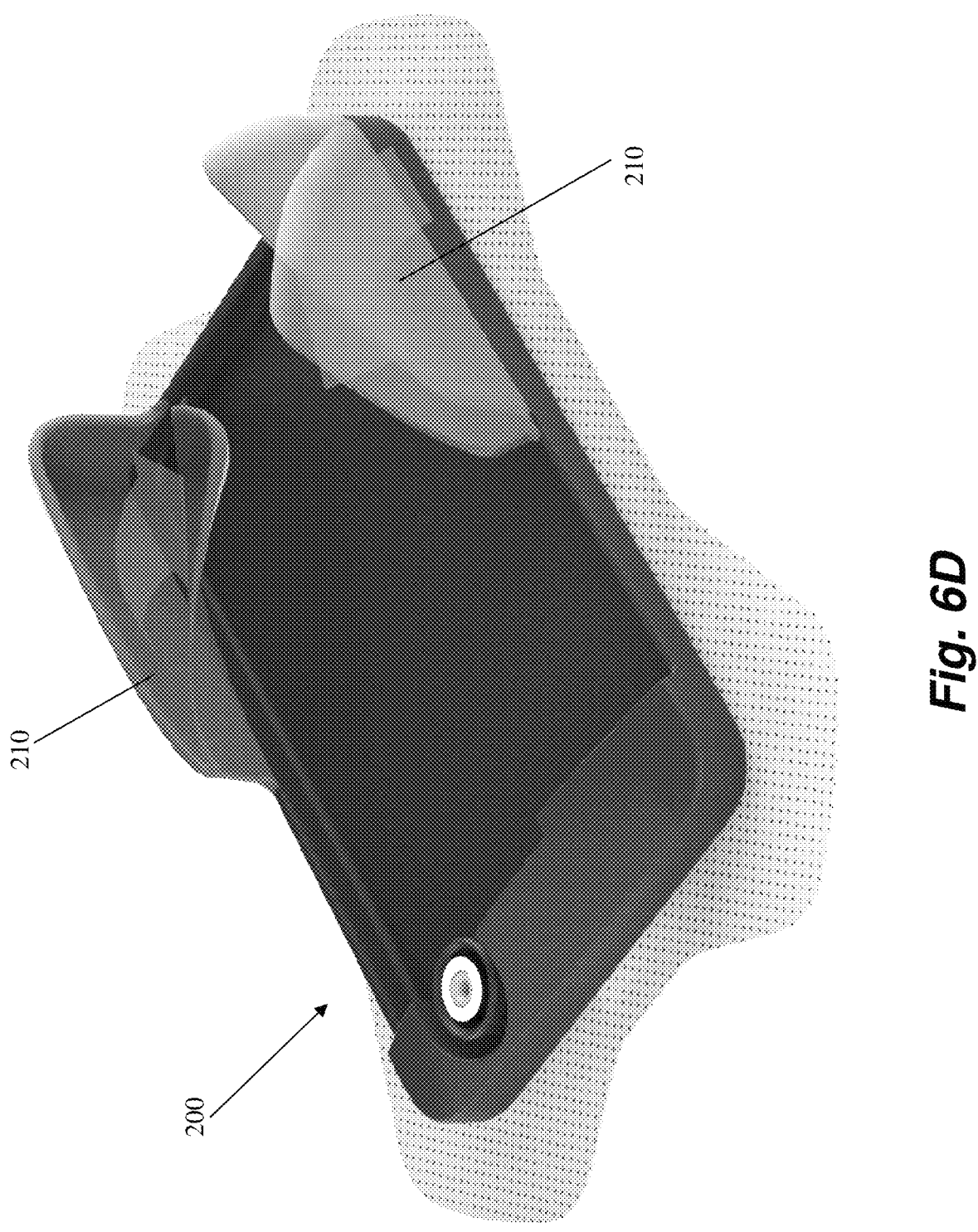

FIGS. 6A-6C depict a pump holder 200 that can be used to releasably contain a user-wearable infusion pump 102 such as the pump depicted in FIGS. 3A-3C. Holder 200 can include a frame 202 disposed on an adhesive patch 204 configured to attach the pump holder 200 directly to the body of a user. Frame 202 can include a base 206 on which the pump rests and a perimeter wall 208 that surrounds a perimeter of a pump disposed on base 206. Perimeter wall 208 can include a pair of retention walls 210 projecting upwardly from perimeter wall 208. Retention walls 210 may wrap around corners of frame 202 and extend generally inwardly (see, FIG. 6B) from frame in order to extend over a portion of a top of pump at the pump corners to aid in retaining the corresponding end of the pump within the frame 202. At the opposite end of the frame 202 from the retention walls 210, the perimeter wall 208 may be thicker in order to accommodate a cannula connector 212 and a clip slot 214. Cannula connector 212 can be defined within a cannula recess 216 sized to accommodate the cannula interface 121 of the cartridge 117 and includes a cannula aperture 218 configured to fluidly connect the outlet 123 of the cartridge 117 with a cannula extending through cannula connector 212 beneath the pump holder 200 and into the user's skin. In practice, a needle can be inserted through cannula aperture 218 to insert the cannula into the skin and then removed prior to inserting the pump 102 onto the pump holder 200, leaving the cannula in place. Slot 214 is an open space defined in perimeter wall 208 with perimeter wall extending slightly inwardly at slot as shown in FIG. 6B. The slot 214 can be configured to provide a snap fit with clip 119 of cartridge 117 to retain the corresponding end of cartridge 117 on pump holder 200 with a downwardly facing planar surface 261 of frame 202 interlocking with the upwardly facing planar surface 157 of locking projection 159 on clip 119. Following insertion, clip 119 can be depressed towards the body of cartridge 117 to release the pump 102 from that portion of the pump holder 200.

Figure 7A:
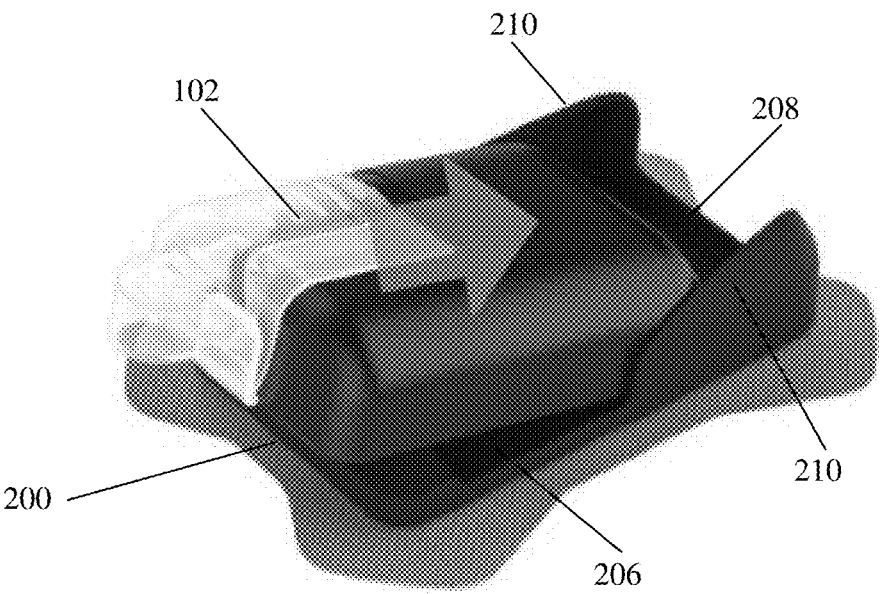
FIGS. 7A-7D depicts the pump system FIGS. 3A-3C inserted into the holder of FIGS. 6A-6C.
Figure 7B:
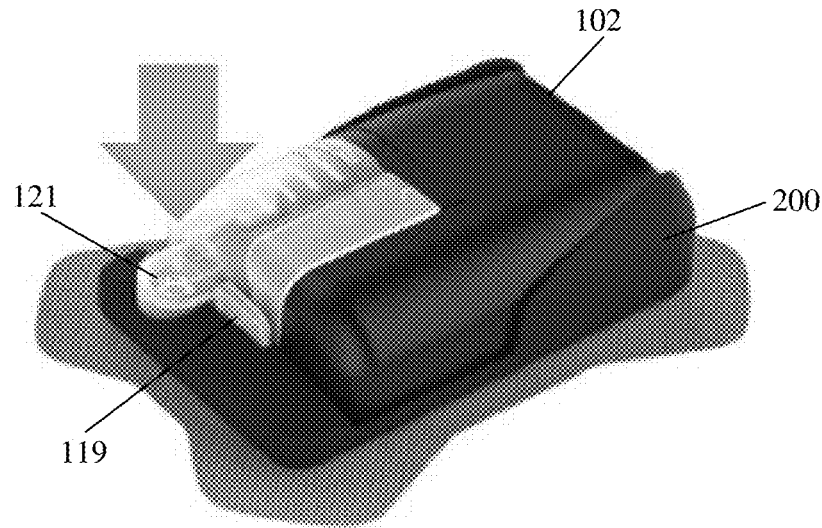
Figures 7C, 7D:
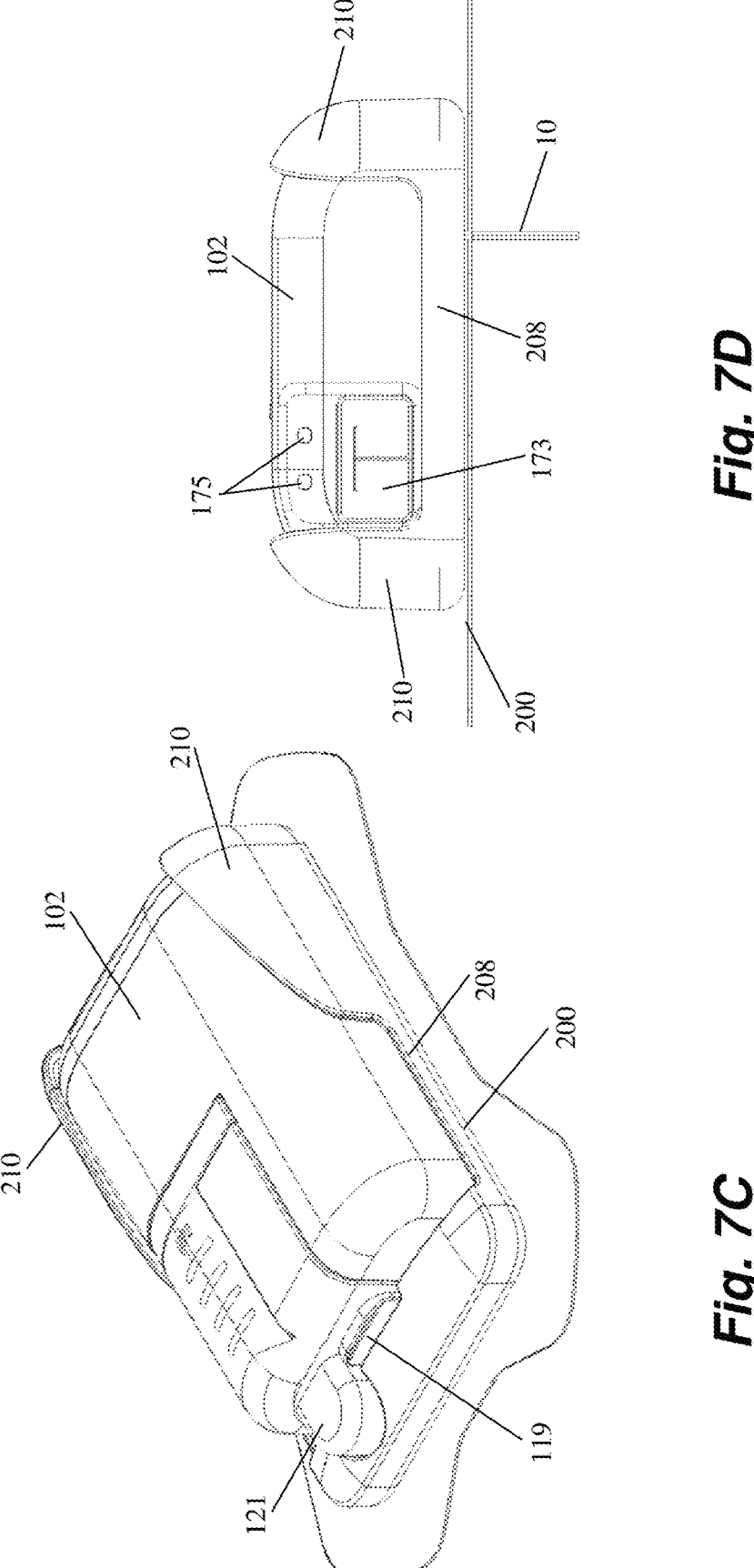

Referring now to FIGS. 7A-7C, pump 102 can be inserted into pump holder 200 by first sliding pump 102 along frame base 206 until the rear of pump 102 reaches the back of the perimeter wall 208 and the rear corners of pump are engaged by the retention walls 210. The front end of pump 102 can then be pushed down onto the pump holder 200. The cannula recess 216 shaped to accommodate the cannula interface 121 of the cartridge 117 ensures proper alignment and insertion of the cartridge outlet 123 with the cannula connector recess 216 and previously inserted cannula. The clip 119 provides a snap fit with the clip slot 214 to releasably secure the front end of the pump 102 on the pump holder 200. As the pump 102 is pushed down onto the pump holder 200, the flexible clip 119, and corresponding locking projection 159, is pushed inwardly by the perimeter wall 208 and then released when the clip 119 is fully seated in the slot 214 to provide the snap fit that interlocks the upwardly facing planar surface 157 of locking projection 159 with the downwardly facing planar surface 261 of frame 202 within slot 214. In this manner, both the rear end of the pump (with retention walls 210) and the front end of the pump (with clip 119) are separately retained on the pump holder 200 to provide a more secure and redundant, yet easily releasable, fit. In addition, as shown in FIG. 7D, the perimeter wall 208 and retention walls 210 are formed to provide easy access to input button 173 and clear viewing of indicator lights 175 of pump 102. FIG. 7D also depicts a cannula 10 extending (from the cannula connector 212) beneath the pump 102 and pump holder 200 into the body of a patient. The front end of the pump 102 can be removed from the pump holder 200 by compressing the clip 119 to release the locking projection 159 from engagement with the downwardly facing frame surface 261 in slot 214 and pulling up on the front end of the pump 102. The pump 102 can then be slid out of the pump holder 200 in the opposite direction of that shown in FIG. 7A to disengage the rear of the pump 102 from the retention walls 210.

Figure 8A:
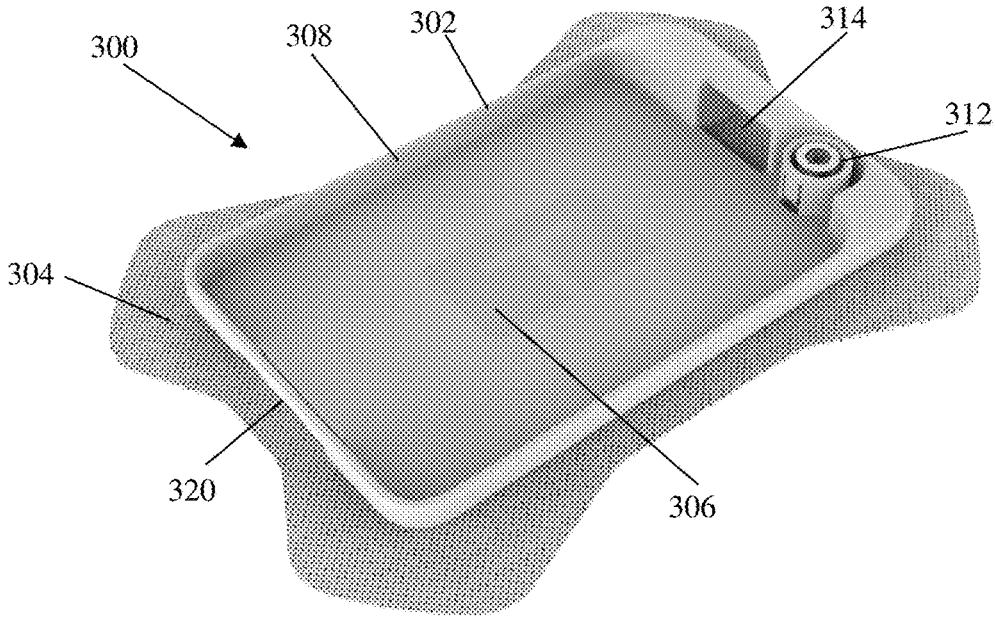
FIGS. 8A-8B depict an embodiment of a pump holder for a pump system according to the disclosure.
Figure 8B:
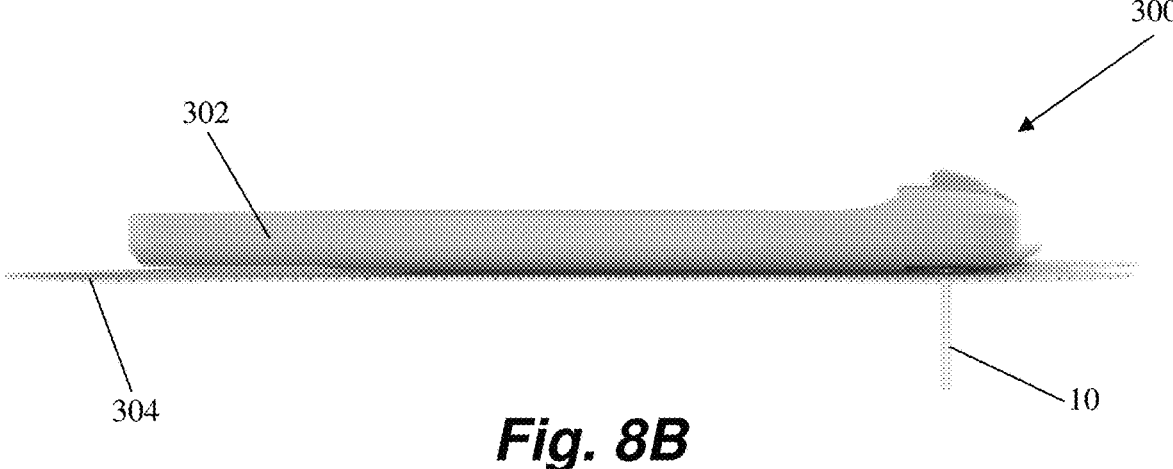
Figures 9A, 9B, 9C:
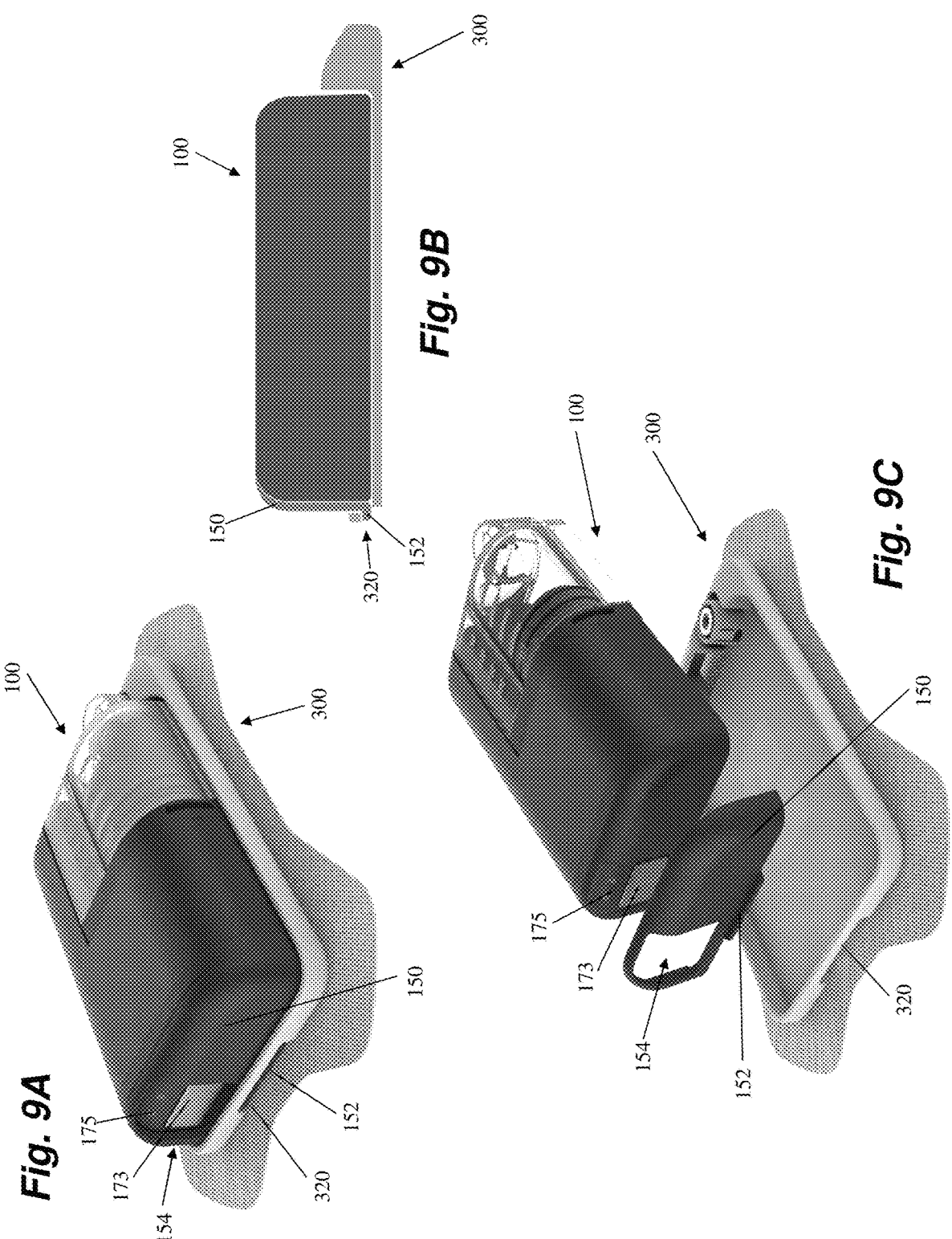
FIGS. 9A-9C depict an embodiment of a pump system according to the disclosure.
Figures 10A, 10B, 10C:
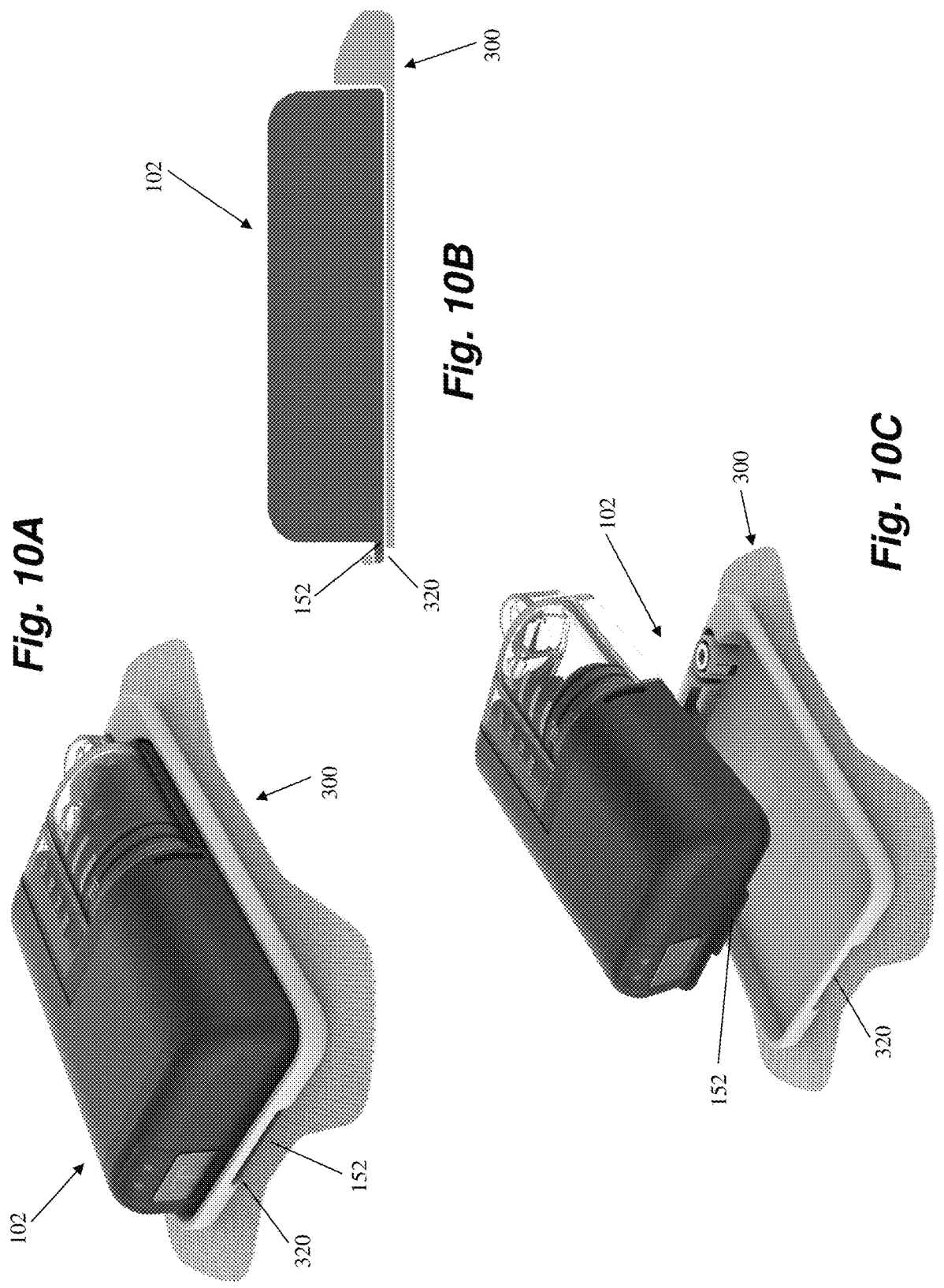
FIGS. 10A-10C depict an embodiment of a pump system according to the disclosure.

FIGS. 8A-8B depict another variation of a pump holder 300 according to the disclosure. Pump holder 300 has a number of features in common with pump holder 200 including a frame 302 disposed on an adhesive patch 304 including a base 306, perimeter wall 308, cannula connector 312 and clip slot 314. Pump holder 300 includes a lower profile tray that does not include upwardly projecting retention walls 210 of pump holder 200. This lower profile can provide an enhanced on-body experience for the user with more discretion and less chance to shag/bump into doorways or other items. Pump holder 300 can include a retention slot 320 through retention wall 308 generally opposing clip slot 314 that aids in retaining a pump 102 in the pump holder 300. Referring to FIGS. 9A-9C, in one embodiment an adapter 150 can be provided for pump 102 and removably affixed to pump with, e.g., an adhesive. Adapter 150 can include a tab 152 that interfaces with slot 320 to aid, along with clip 119 and clip slot 314 at the opposite end of pump and holder, in retaining pump 102 on pump holder 300. Adapter can further include a window 154 that enables pump button 173 to be accessed and indicator lights 175 to be viewed with adapter 150 attached to pump 102. In practice, to secure the pump 102 on the holder 300, the user can first insert the tab 152 into the retention slot 320 and then pivot the pump 102 down to snap fit the clip 119 into the clip slot 314 as described above. The pump 102 can similarly be removed as described above by depressing clip 119 to release the interlock of the pump 102 with clip slot 314. FIGS. 10A-10C depict a similar embodiment, in which there is no adapter 150 and instead the tab 152 is unitarily formed as part of the body of drive unit 118 of pump 102.

Figures 11A, 11B, 11C:
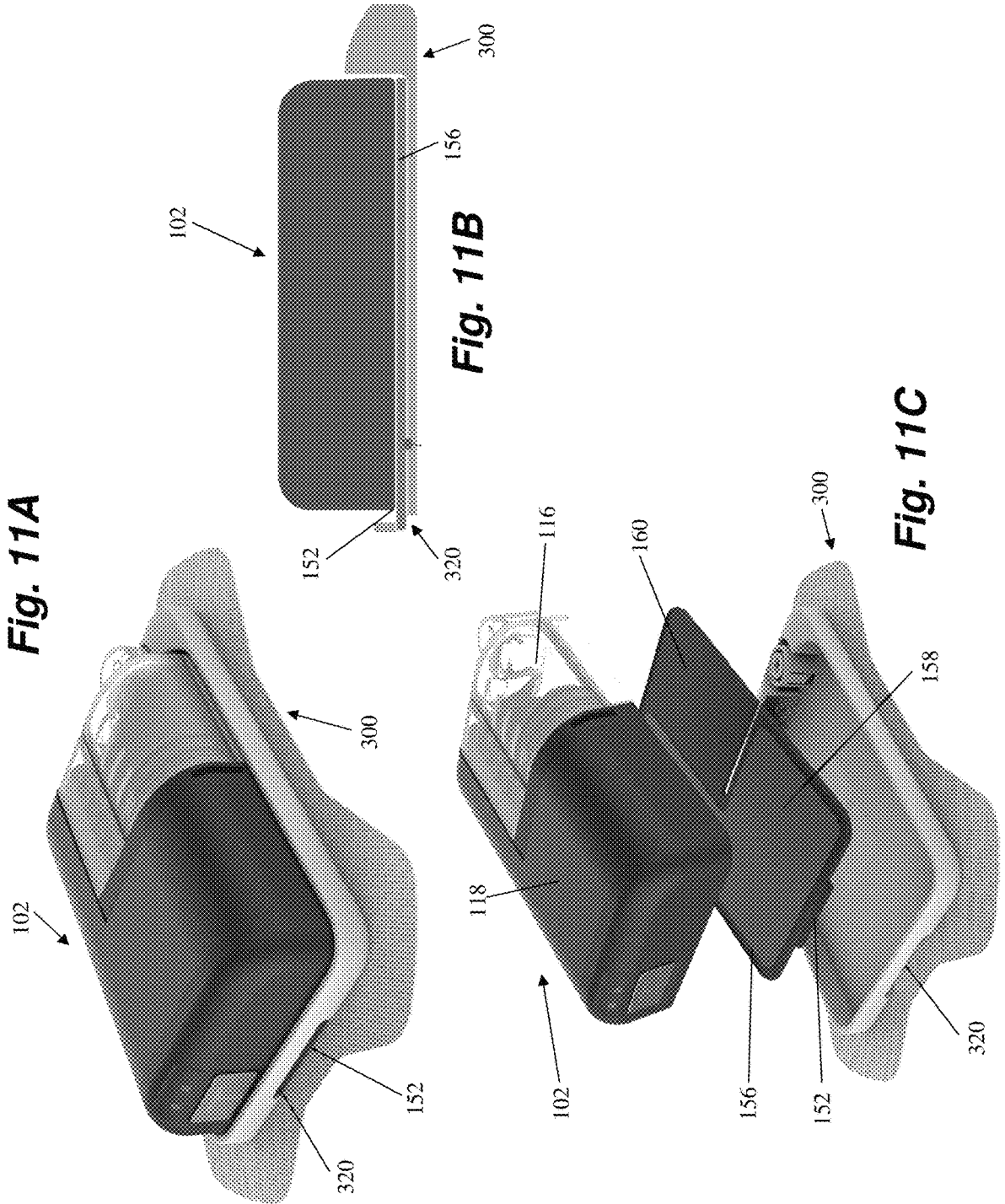
FIGS. 11A-11C depict an embodiment of a pump system according to the disclosure.
Figures 12A, 12B, 12C:
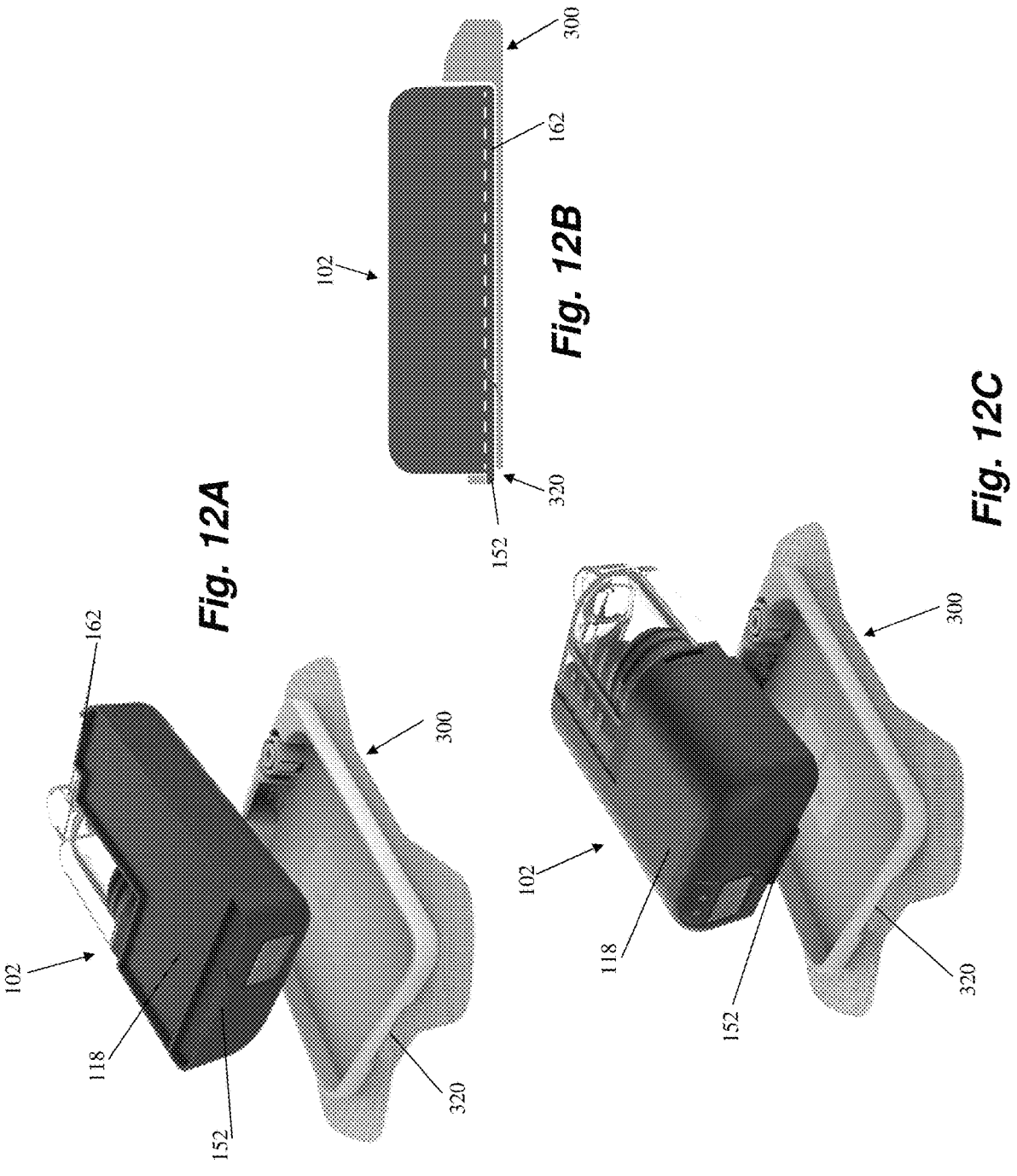
FIGS. 12A-12C depict an embodiment of a pump system according to the disclosure.

FIGS. 11A-11C depict an embodiment of pump holder 300 that includes an adapter 156 that can be affixed to a bottom surface of pump 102. Adapter 156 can include a partial adhesive patch 158 that leaves a cartridge portion 160 of adapter 156 not adhered to the cartridge 116 of pump 102 that allows the adapter 156 to flex to enable rotation of cartridge 116 for installation and removal of the cartridge from the drive unit 108 (because if the adapter 156 were adhered to the cartridge, the cartridge could not be detached from the drive unit 108 with the adapter 156 attached). Adapter 156 similarly includes a projection 152 that interfaces with the retention slot 320 in pump holder 300 as described above. FIGS. 12A-12C disclose a similar embodiment, in which pump 102 is modified to essentially incorporate adapter 156 by providing a wall 162 around drive unit that provides a taller pump and includes a projection 152 that interfaces with retention slot 320. In other embodiments, projection 152 can be provided on pump 102 without the wall 162 increasing the height of the pump and the frame of the holder 300 can be modified from the previous embodiment to be shorter.

Figures 13A, 13B, 13C:
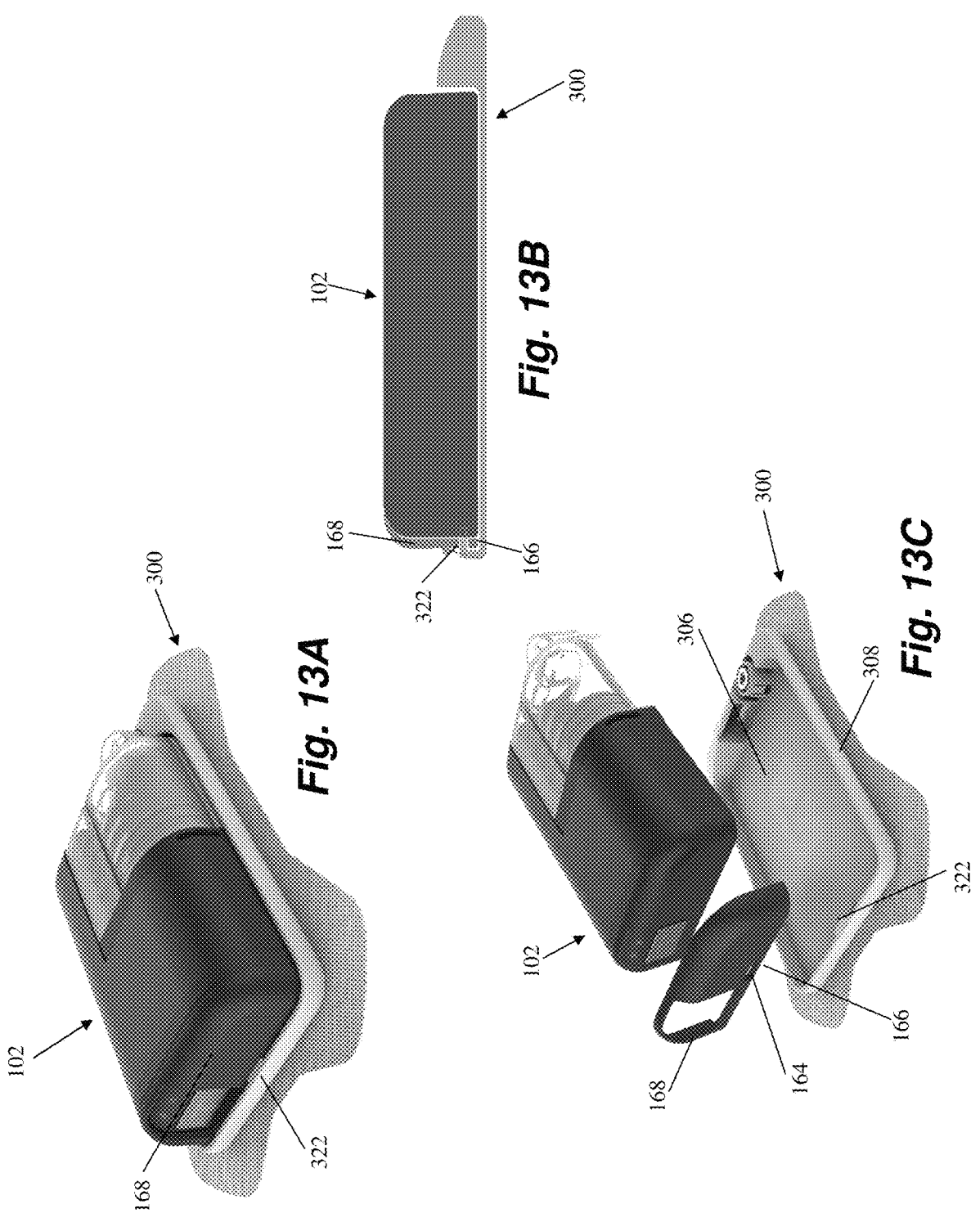
FIGS. 13A-13C depict an embodiment of a pump system according to the disclosure.
Figures 14A, 14B, 14C:
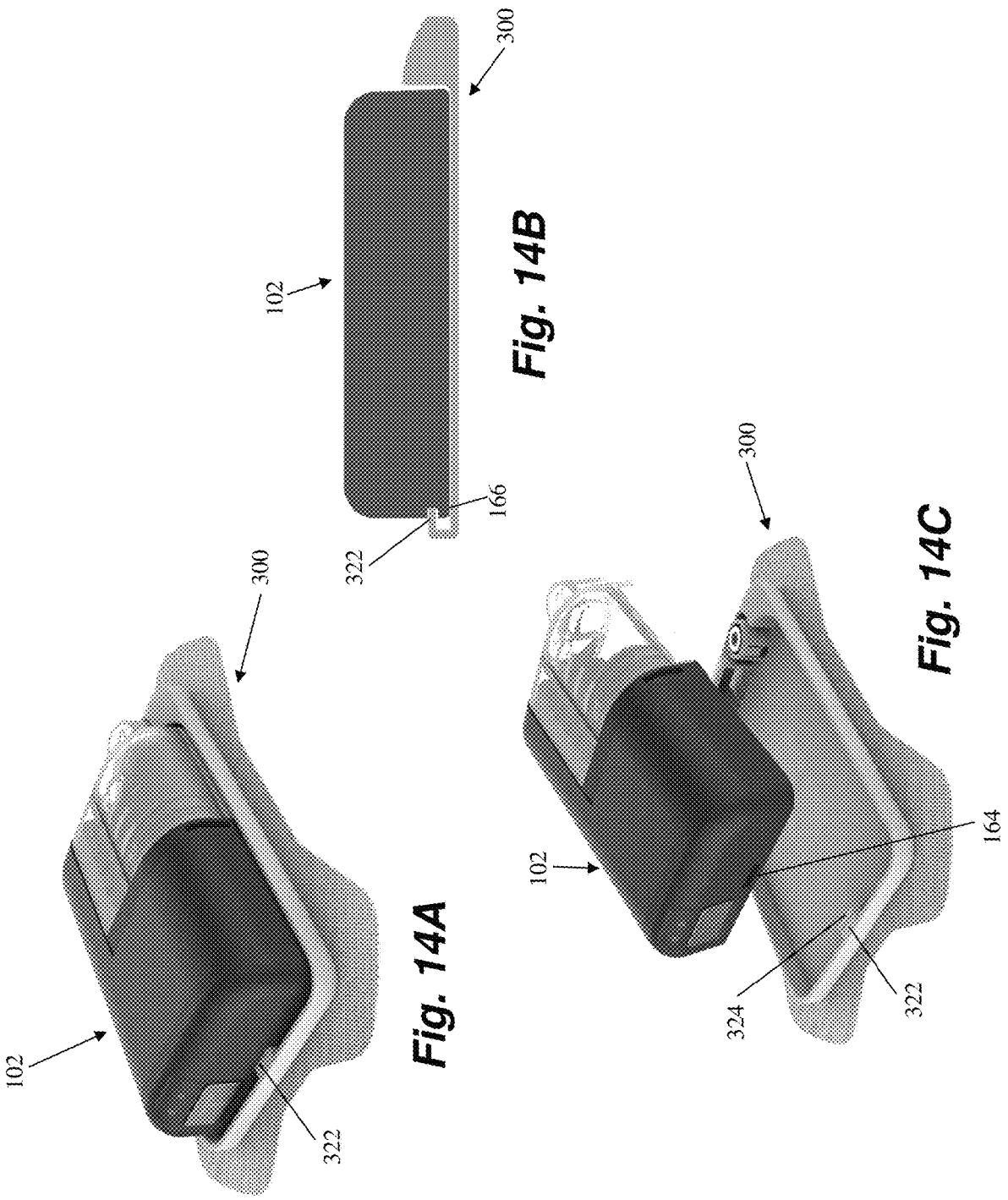
FIGS. 14A-14C depict an embodiment of a pump system according to the disclosure.
Figures 15A, 15B, 15C:
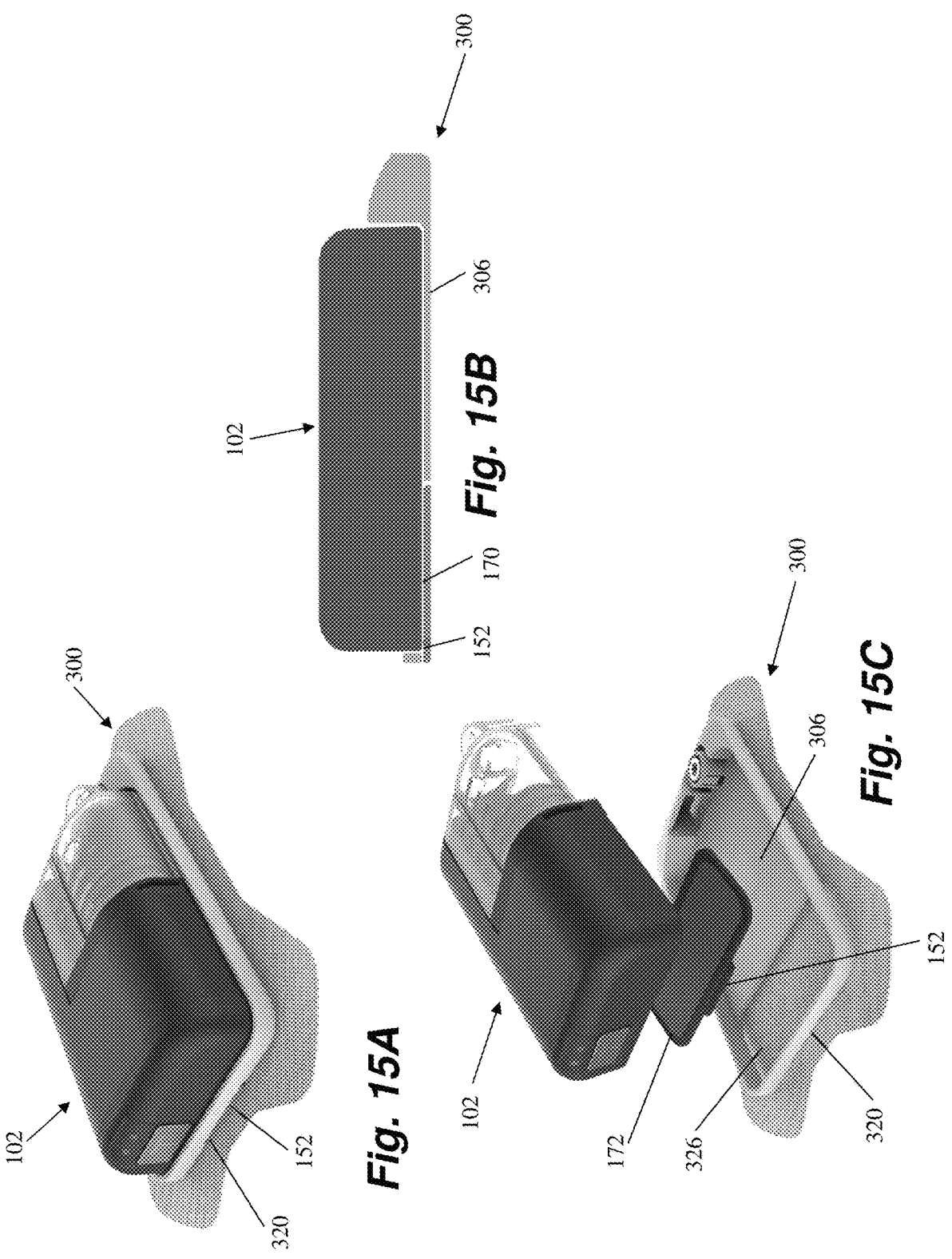
FIGS. 15A-15C depict an embodiment of a pump system according to the disclosure.

FIGS. 13A-13C and 14A-14C depict an embodiment of pump holder 300 in which the pump holder 300 includes the projection 322 and the pump 102 includes the retention slot 164. Projection 322 can extend inwardly from retention wall 308 at a height leaving a space between projection 322 and frame base 306 in which a bottom portion 166 can be releasably held when pump 102 is inserted onto holder 300. In the embodiment of FIGS. 13A-13C, the retention slot 164 of pump 102 is provided by a separate adapter 168 that can be attached to pump 102 similar to adapter 150 described above whereas in the embodiment of FIGS. 14A-14C the retention slot 164 can be unitarily molded into the pump 102 itself. In another embodiment, retention slot 164 can be a metal insert that is insert molded into pump 102. In embodiments, projection 322 can have a breakaway portion 324 that enables tab to be a longer length for interfacing with a retention slot 164 formed in the pump and a shorter length with breakaway portion removed for interfacing with a retention slot 164 formed by adapter 168. In other embodiments, two tray types can be provided having different length projections 322. Similar to the previous embodiments, retention slot 164 can be inserted onto projection 322 and then the pump pivoted down to interlock clip 119 in clip slot 314 to retain the pump 102 on the holder 300.

Figures 16A, 16B, 16C:
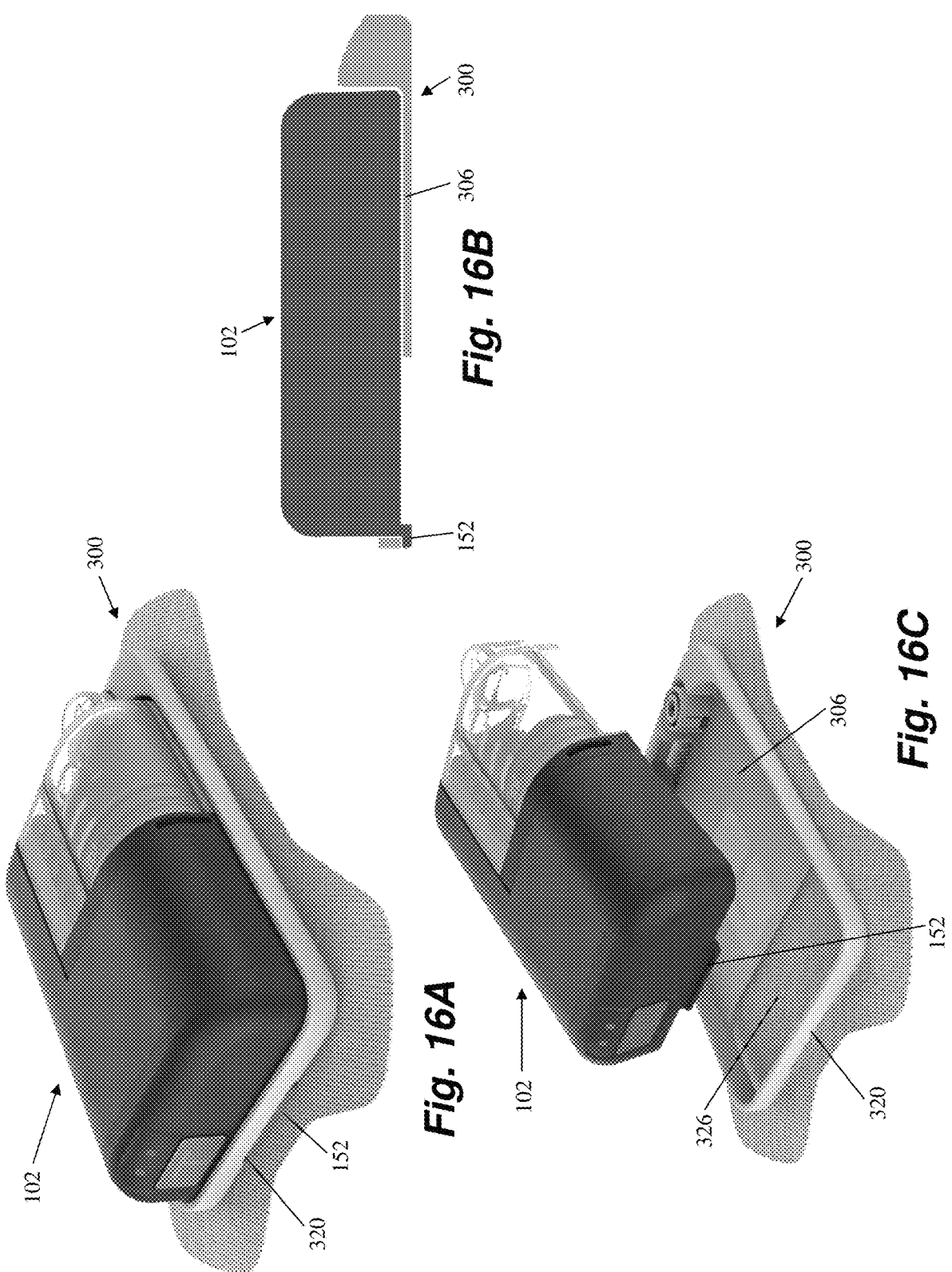
FIGS. 16A-16C depict an embodiment of a pump system according to the disclosure.

FIGS. 15A-15C and 16A-16C depict another embodiment of pump holder 300 including a retention slot 320 and a cutout portion 326 in frame base 306. The embodiment of FIGS. 15A-15C includes an adapter 172 that can be affixed to a bottom of pump 102 sized to be received in cutout portion 326 and that aligns with base 306 that includes the projection 152 received in retention slot 320. FIGS. 16A-16C depict an embodiment in which the projection 152 is unitarily molded onto pump 102 (and, as can be seen in FIG. 16B, use of the same tray results in a space between pump 102 bottom aver the cutout portion 126).

Although the previous embodiments have generally contemplated use of adapters formed of a similar plastic material to pump body (though other materials such as metal could be used), in some embodiments adapters can be formed of a sturdier material, including a metal such as steel.

Figures 17A, 17B, 17C:
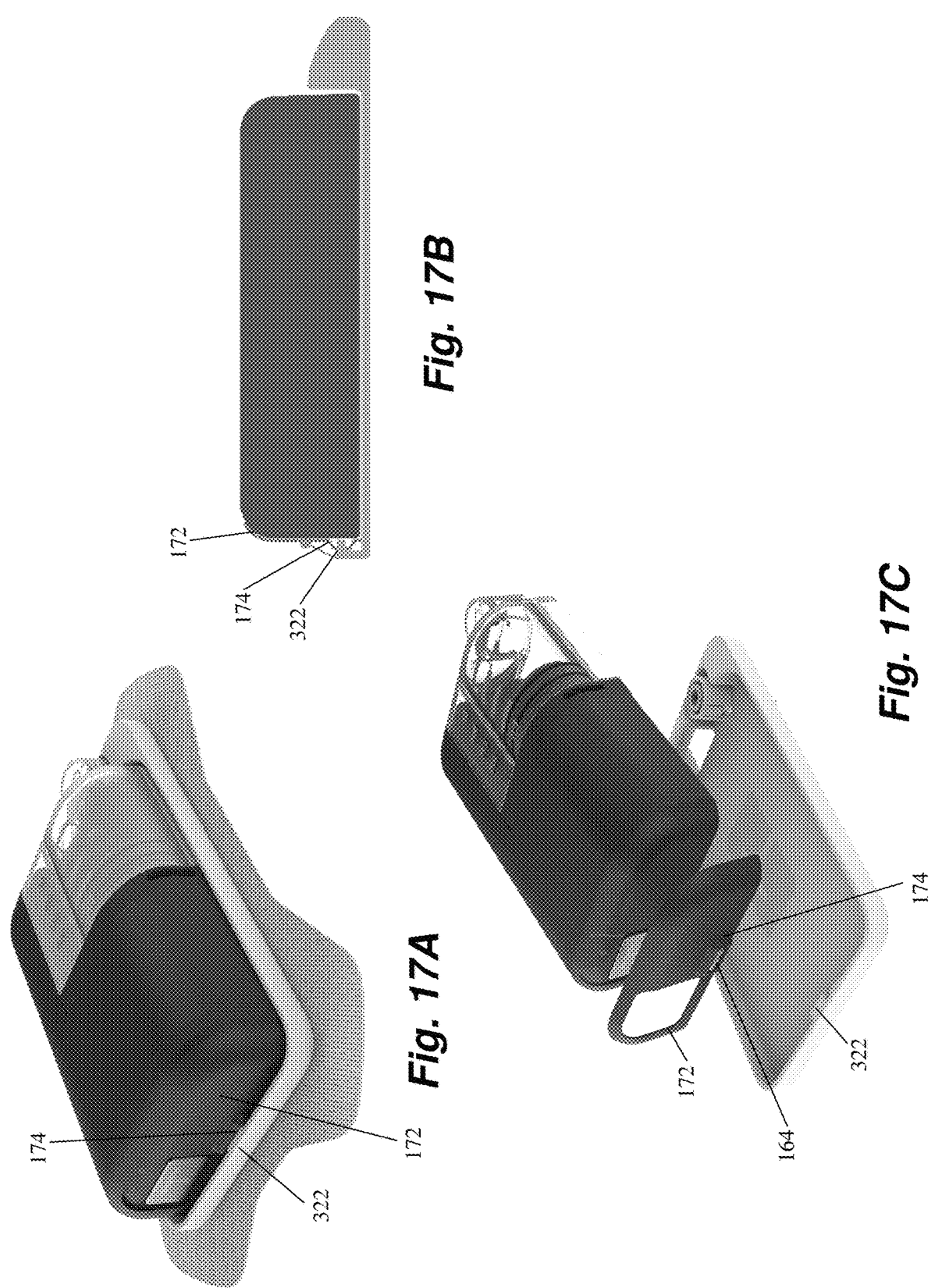
FIGS. 17A-17C depict an embodiment of a pump system according to the disclosure.
Figures 18A, 18B, 18C:
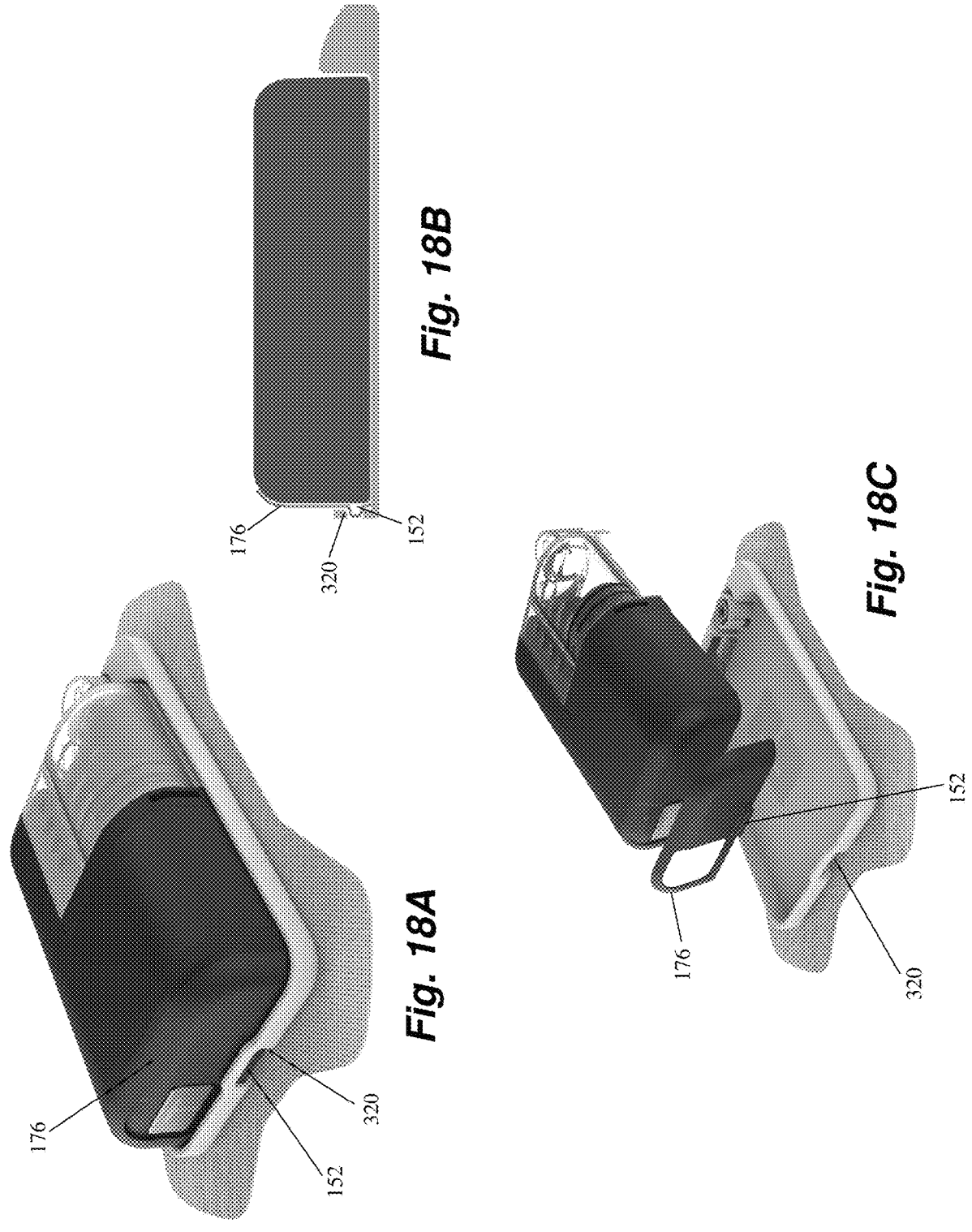
FIGS. 18A-18C depict an embodiment of a pump system according to the disclosure.
Figures 19A, 19B, 19C:
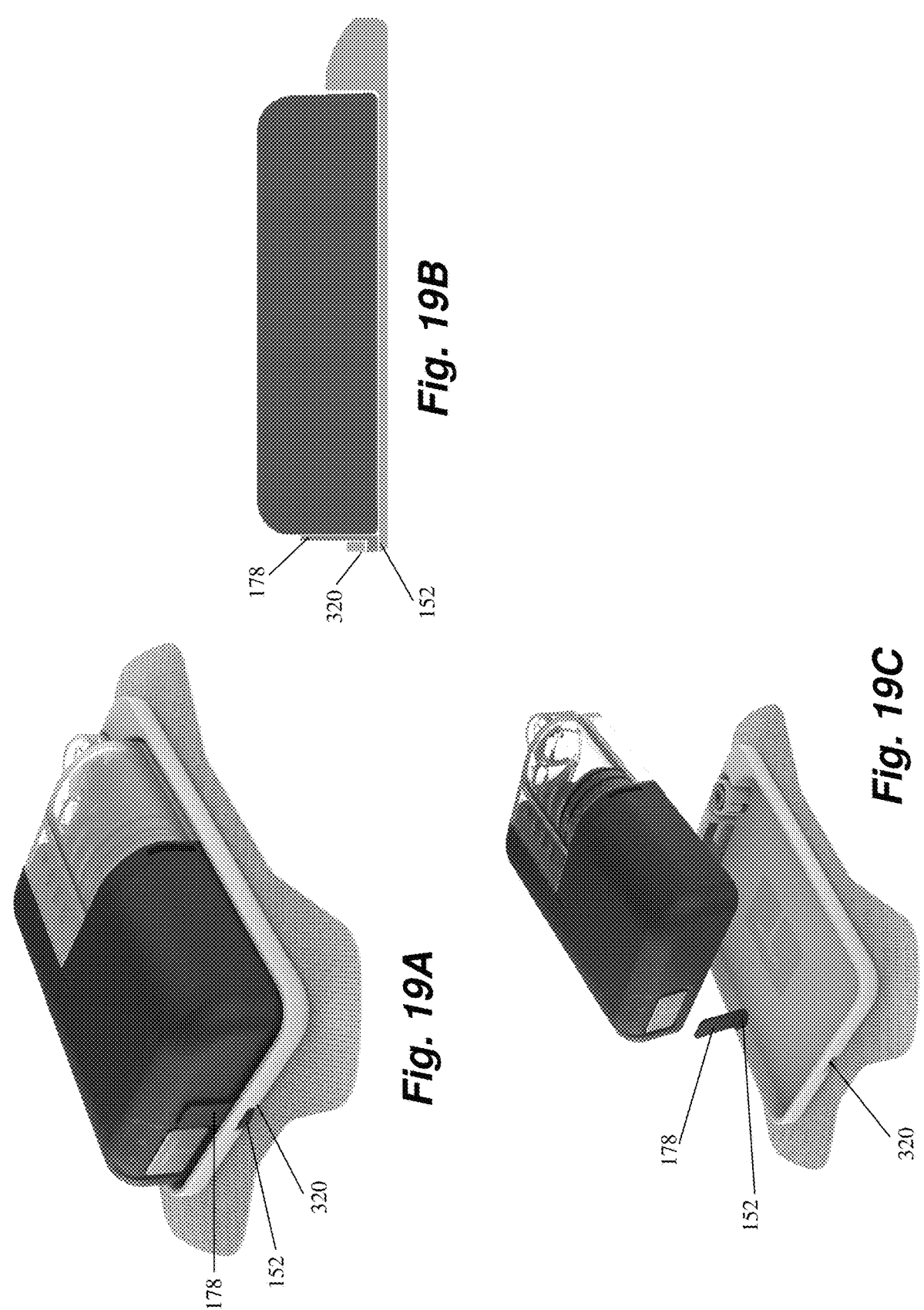
FIGS. 19A-19C depict an embodiment of a pump system according to the disclosure.

FIGS. 17A-17C depict an adapter 172 that can be formed of a metal such as steel including a retention slot 164 that interfaces with a tab 322 on pump holder 300 similar to embodiments described above. In this embodiment, adapter 172 can further include a flange 174 around slot 164 that further aids in pump retention. FIGS. 18A-18C depict an embodiment of a metal adapter 176 having a tab 152 that interfaces with a retention slot 320 in frame similar to the corresponding embodiments described above. Tab 152 of metal adapter 176 can be narrower in width than the corresponding tab 152 of the adapters described above. FIGS. 19A-19C depict another embodiment of an adapter 178 having a tab 152 for interfacing with slot 320 and having a smaller profile and that can be metal, plastic or other material. Metal adapters provide increased strength and wear resistance that can better withstand use over the approximately 5 years that a pump may be in use.

Figure 20:
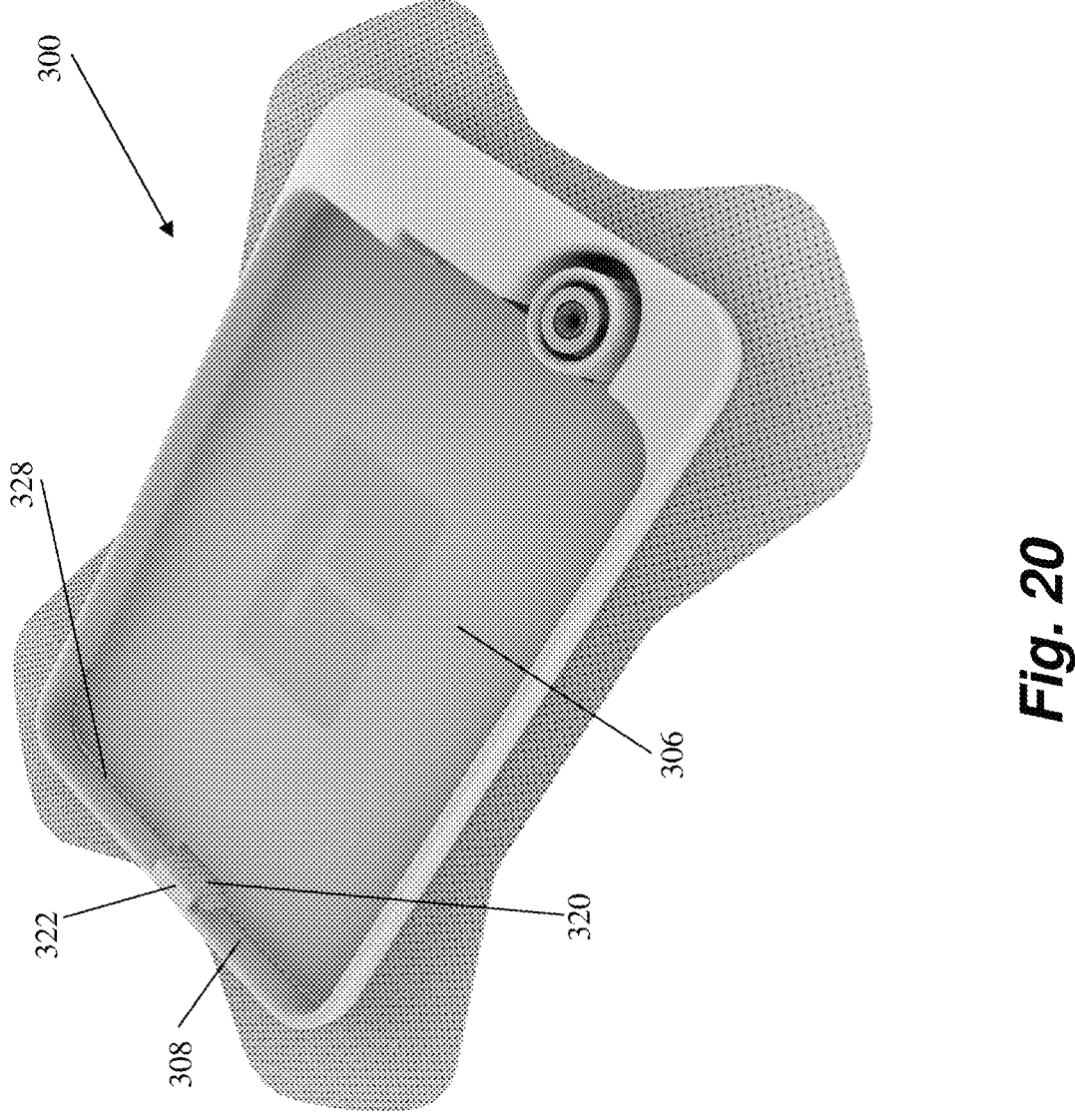
FIG. 20 depicts an embodiment of a pump holder for a pump system according to the disclosure.
Figure 21A:
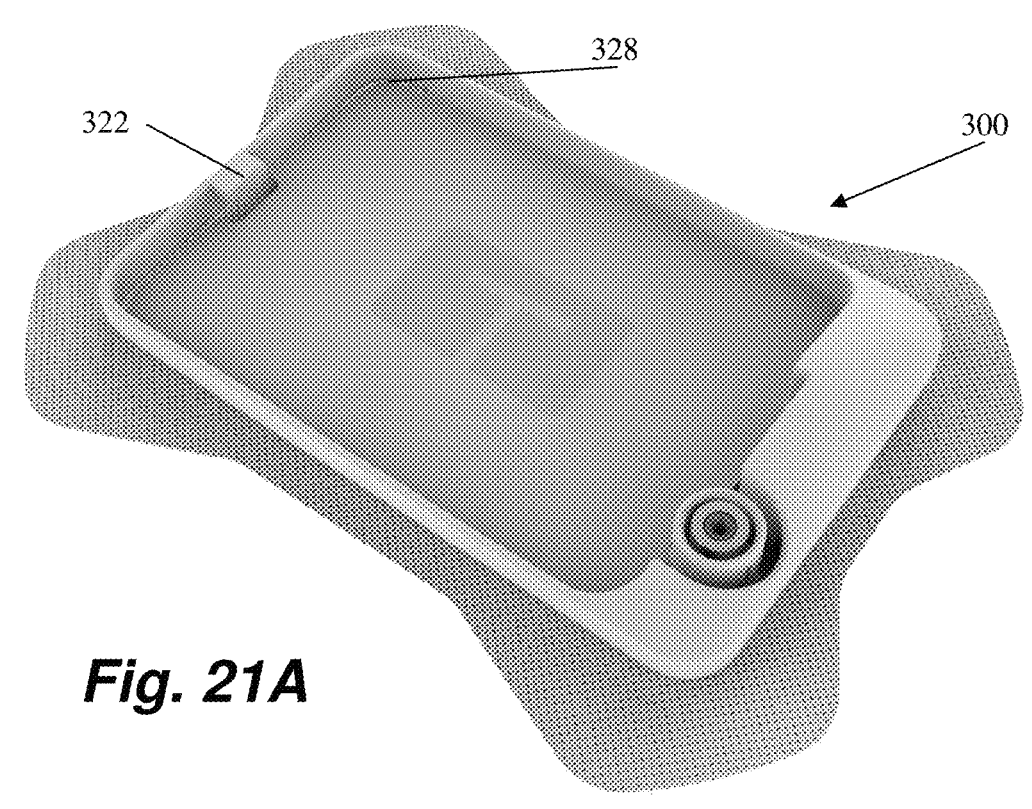
FIGS. 21A-21B depict an embodiment of a pump holder for a pump system according to the disclosure.
Figure 21B:
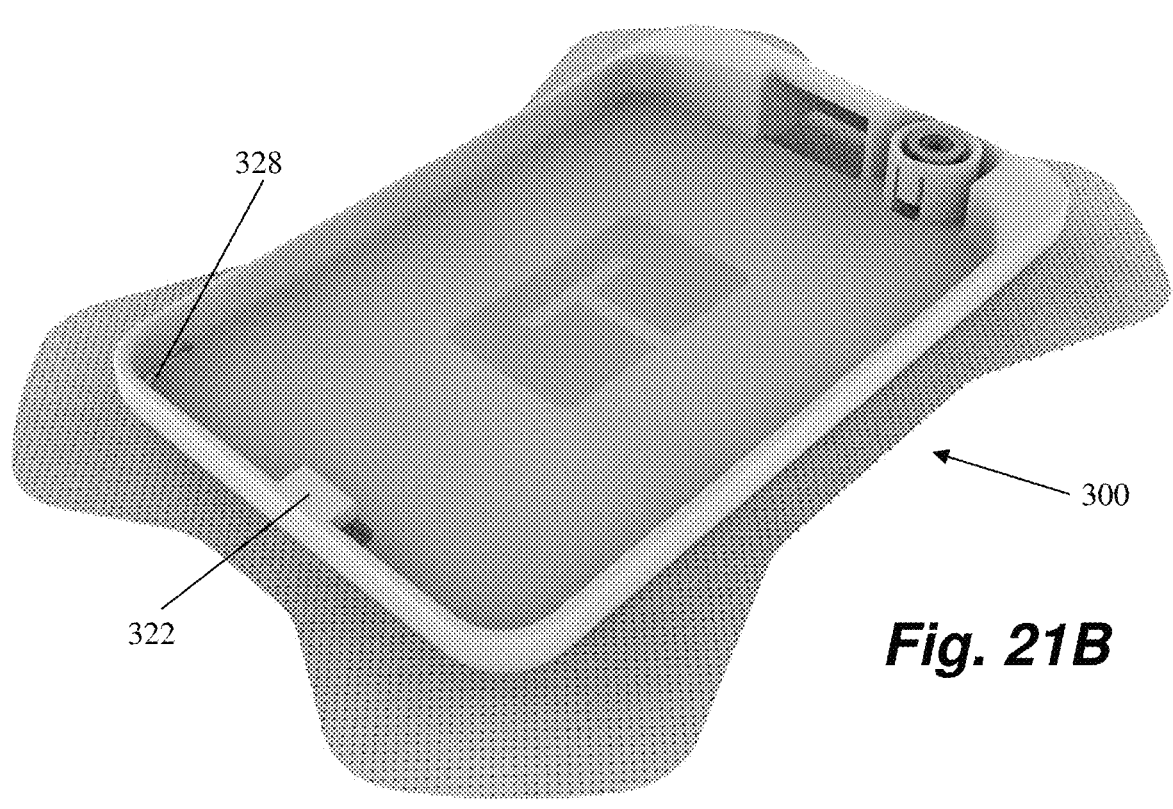

FIG. 20 depicts an embodiment of a pump holder 300 that combines aspects of previous embodiments with both a retention slot 320 for interfacing with a projection on a pump and a tab 322 for interfacing with a retention slot in a pump. In some embodiments, such a configuration provides flexibility to interface with a pump having a retention slot formed therein or with such a pump having an adapter with a projection attached, as described above. The embodiment of FIG. 20 also includes a relief cut 328 providing a gap between the frame bottom 306 and the retention wall 308 that enables the wall 308 to flex to aid in insertion and removal of a pump from the pump holder 306. In the depicted embodiment, the relief cut 328 extends the entirely of the back wall of the retention wall and around the adjacent corners. FIGS. 21A-21B depict a similar embodiment including only a tab 322 and not a retention slot and also including the relief cut 328 that enables the back wall of the retention wall 328 to flex when interfaced with the pump (and/or pump adapter).

Figures 22A, 22B, 22C:
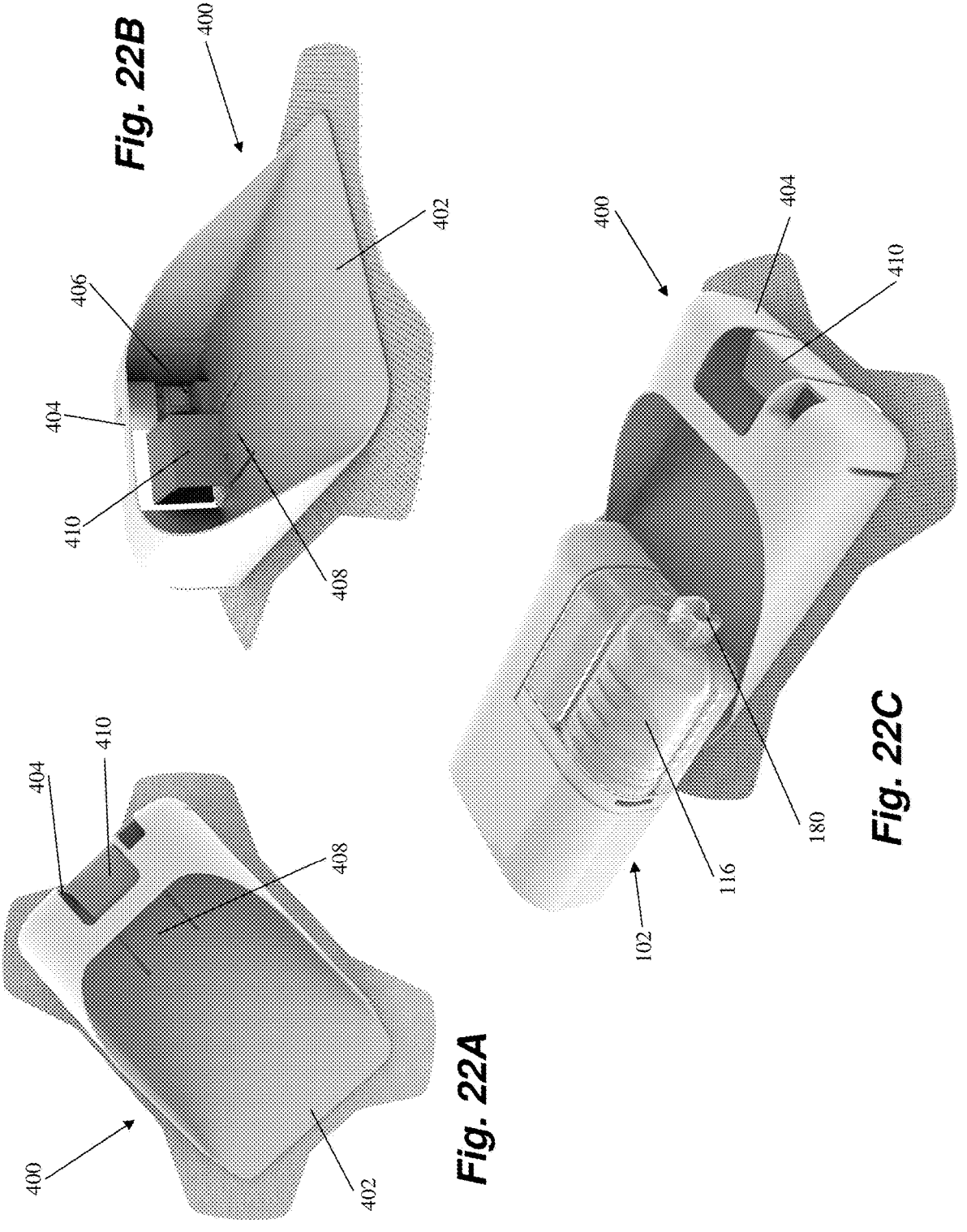
Figures 22D, 22E, 22F:
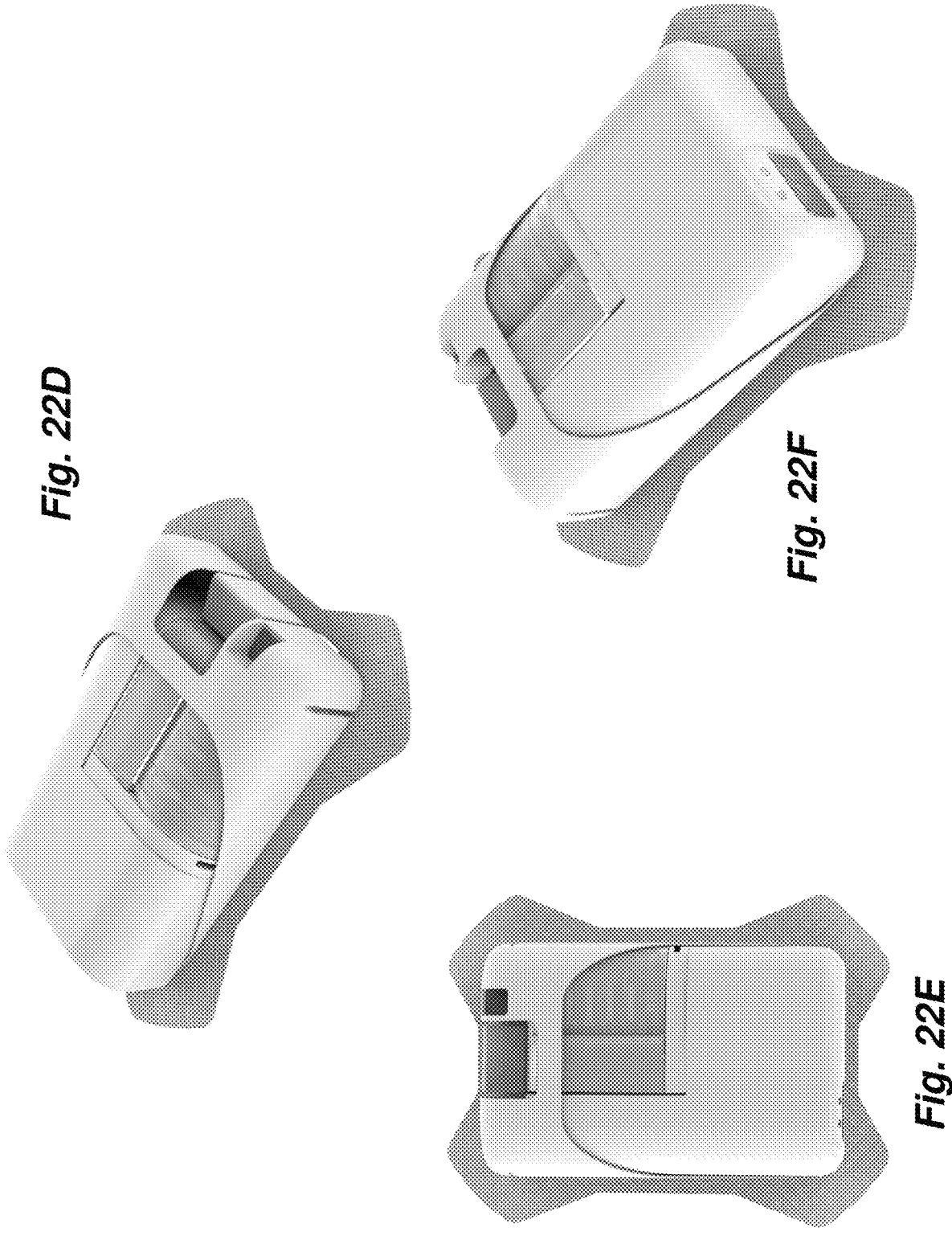

FIGS. 22A-22H depict another embodiment of a pump holder 400 that includes a horizontal, sliding engagement with pump 102 rather than the vertical, pivoting engagement primarily described above. In this embodiment, pump holder 400 includes a first open end 402 and a second pump engagement end 404 including a cannula connector 406 configured to slidingly receive a corresponding engagement portion 180 on pump cartridge 116 and a locking tab 408 that releasably locks onto an underside of cartridge 116 to retain the pump 102 on the holder 400. A latch 410 can be disposed on holder 400 and be accessible from the pump engagement end 404 to disengage the locking tab 408 from the pump 102. FIGS. 22D-22F depict the pump 100 retained on holder 400. To release the pump 102 from the holder 400, arrows 1-2 in FIG. 22G depict where a user will press down on latch 410 of holder in direction (1) and push on the exposed portion of pump in direction (2) in a combined motion to disengage the pump 102 from the holder 400.

Figures 25A, 25B:
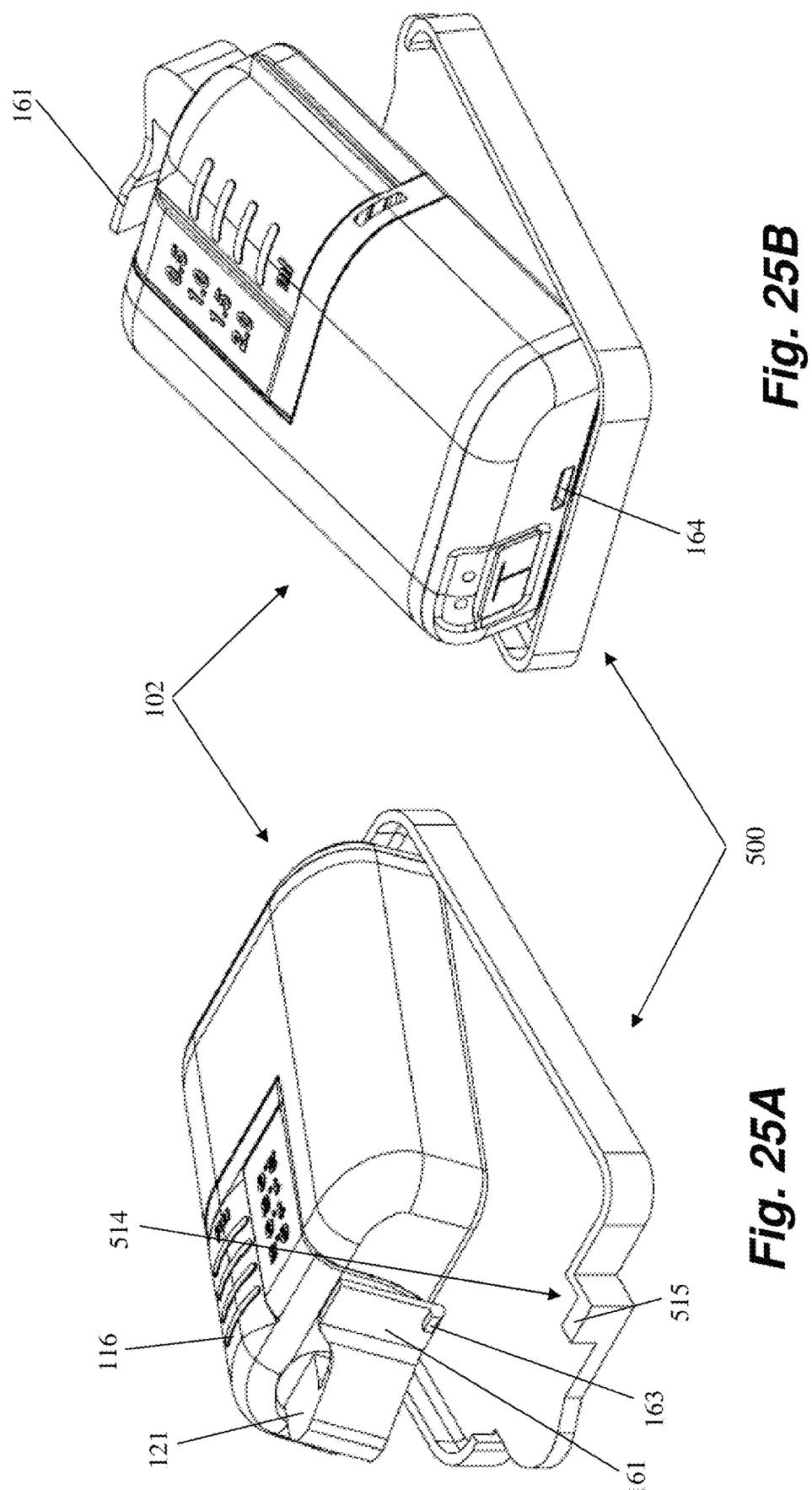
FIGS. 25A-25D depict an embodiment of a pump holder for a pump system according to the disclosure.
Figures 25C, 25D:
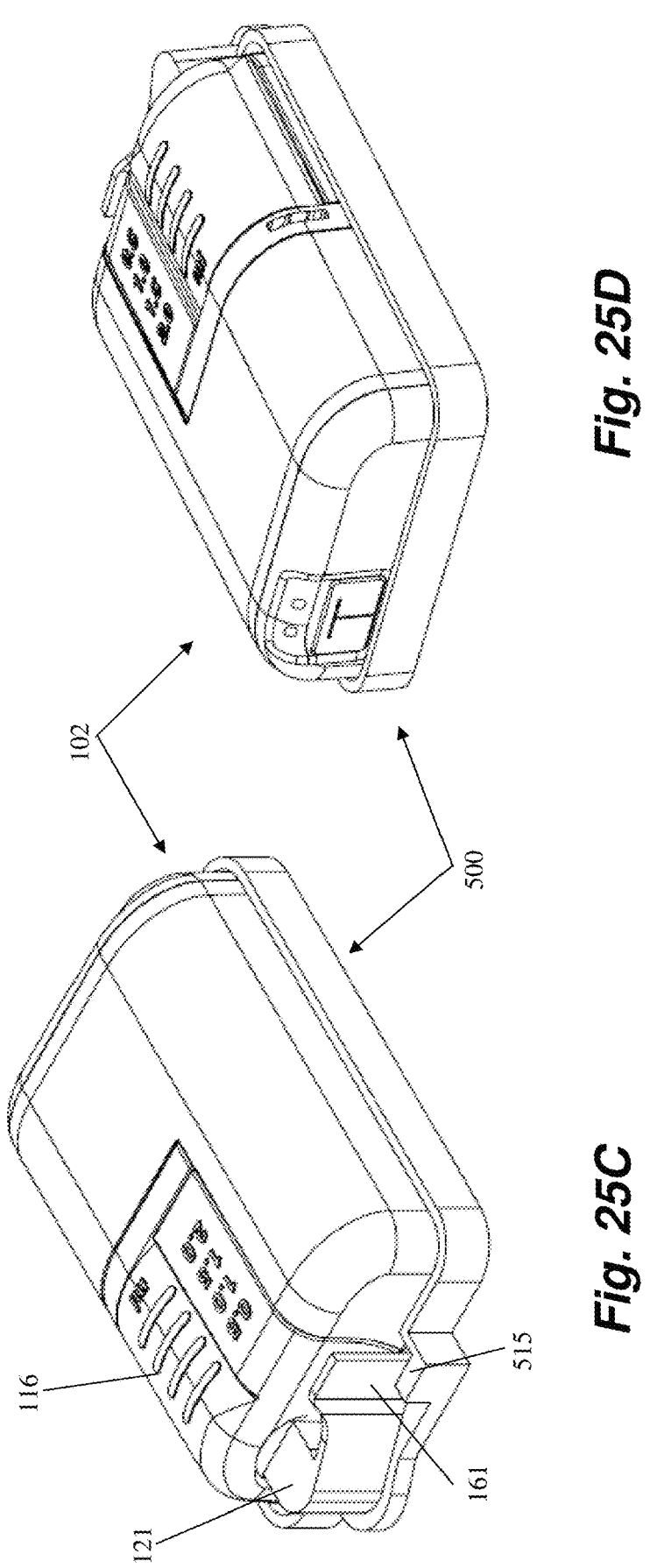

FIGS. 25A-25D depict a further embodiment of a pump holder 500 for a pump system according to the disclosure. In this embodiment, tray 500 can include a projection (not pictured, but similar to previous embodiments) that interfaces with a slot 164 on pump 102. After inserting slot 164 on pump 102 onto projection with the pump 102 at an angle such as depicted in FIGS. 25A-25B, the pump 102 can be pivoted downward to engage a flexible clip 161 on the pump cartridge 116 with a recess 514 in tray 500. In this embodiment, clip 161 can include a locking projection 163 that snaps into recess 514 after clip 161 is released and interlocks with a ledge 515 adjacent recess 514 to releasably hold the clip 161 and retain the pump 102 on the holder 500. A needle in cannula interface 121 of pump cartridge 116 is vertically inserted into a corresponding septum in holder 500 as the pump 102 is pivoted downward with the needle being perpendicular to the holder 500 following insertion to facilitate delivery of medicament beneath holder 500. To release the pump 102 from the holder 500, the clip 161 can be depressed to disengage the projection 163 from the ledge 515 to enable the pump to pivot upwardly and remove the slot 164 from the projection at the other end of the holder 500. Although not pictured, holder 500 may further include an adhesive patch to attach the holder 500 to a body of a user as with previous embodiments.

Figures 26A, 26B:
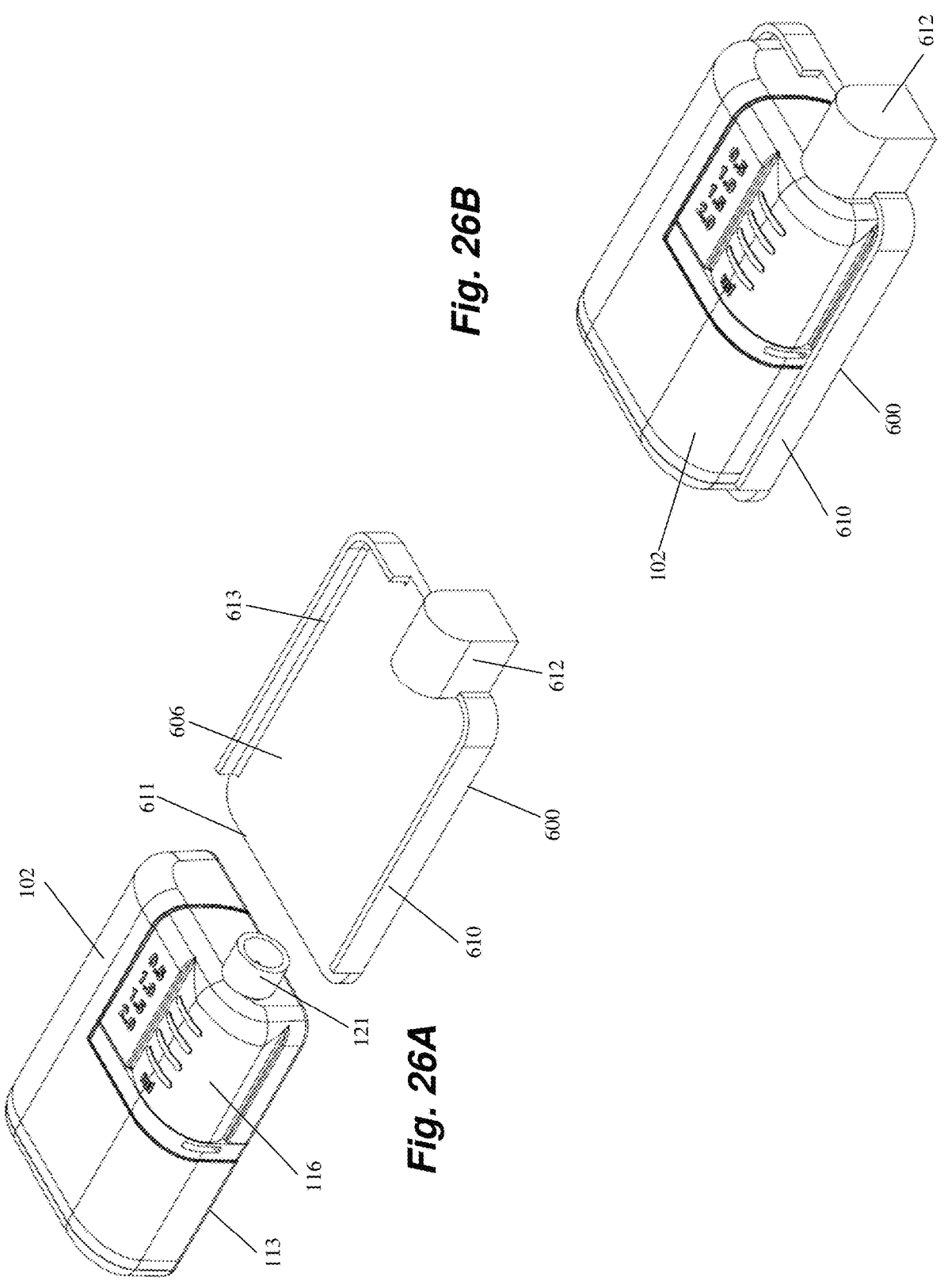
FIGS. 26A-26B depict an embodiment of a pump holder for a pump system according to the disclosure.

FIGS. 26A-26B depict an embodiment of a pump holder 600 for a pump system according to another embodiment of the disclosure. In this embodiment, perimeter wall 610 wall of holder 600 includes an open end 611 that enables pump to be placed on base 606 of holder and slid horizontally to engage pump 102 with holder 600. A needle in cannula interface 121 of pump cartridge 116 is therefore horizontally engaged with a corresponding feature in a connector 612 of holder 600 to facilitate delivery of medicament. In some embodiments, the perimeter wall 610 of holder 600 can include projections or grooves that align with corresponding grooves or projections on pump 102 to guide pump as it is inserted onto holder 600. In the depicted embodiment, an elongate rail 613 projects inwardly from retention wall 610 along both sides of base 606 that interfaces with corresponding elongate grooves 113 in pump 102. In various embodiments, a retention feature on the tray can latch into one or more of the front, rear, side and bottom surfaces of the pump 102 to releasably retain the pump on the holder. An adhesive patch can attach the holder 600 to a body of a user as with previous embodiments.

Figures 27A, 27B:
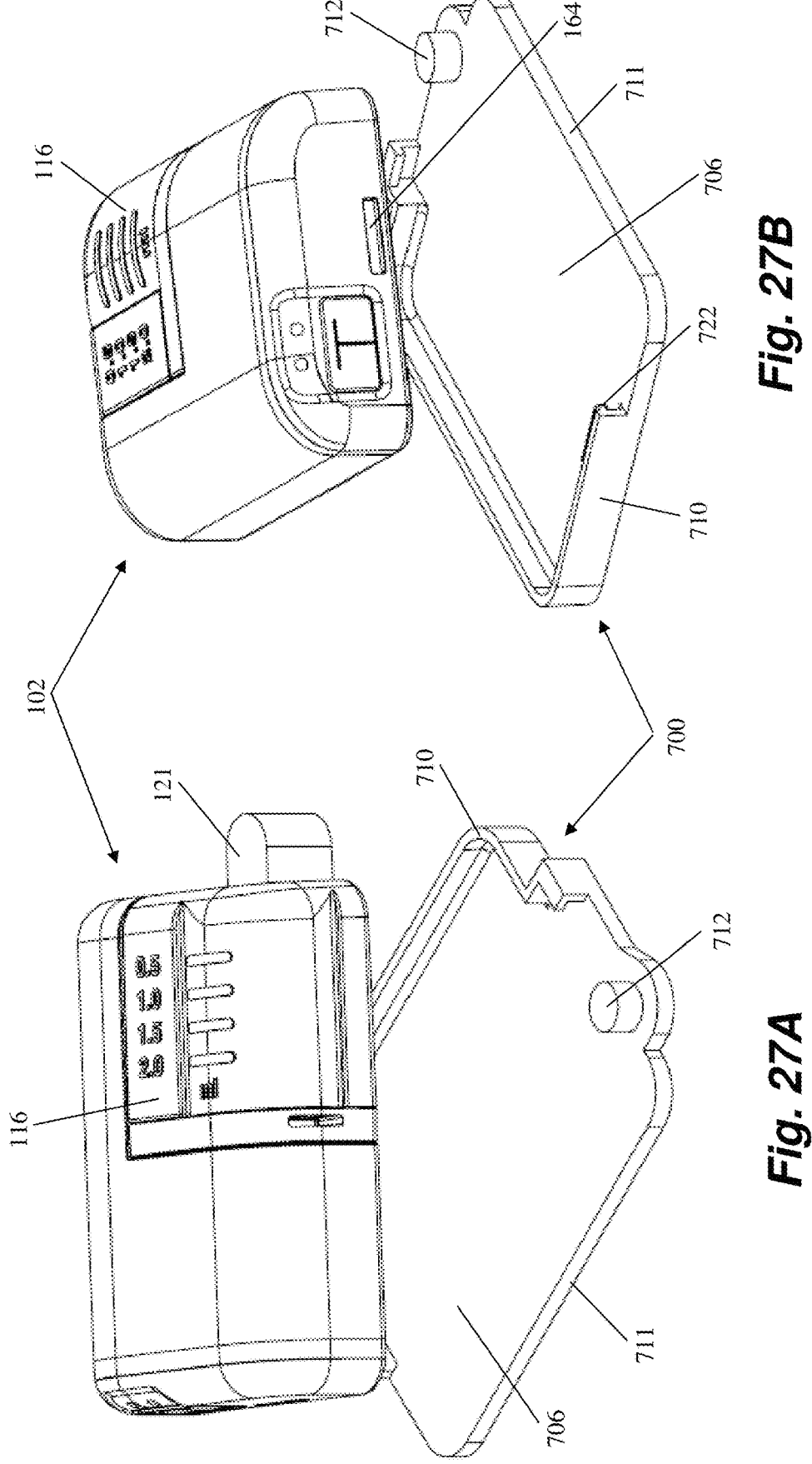
FIGS. 27A-27F depict an embodiment of a pump holder for a pump system according to the disclosure.
Figure 27D:
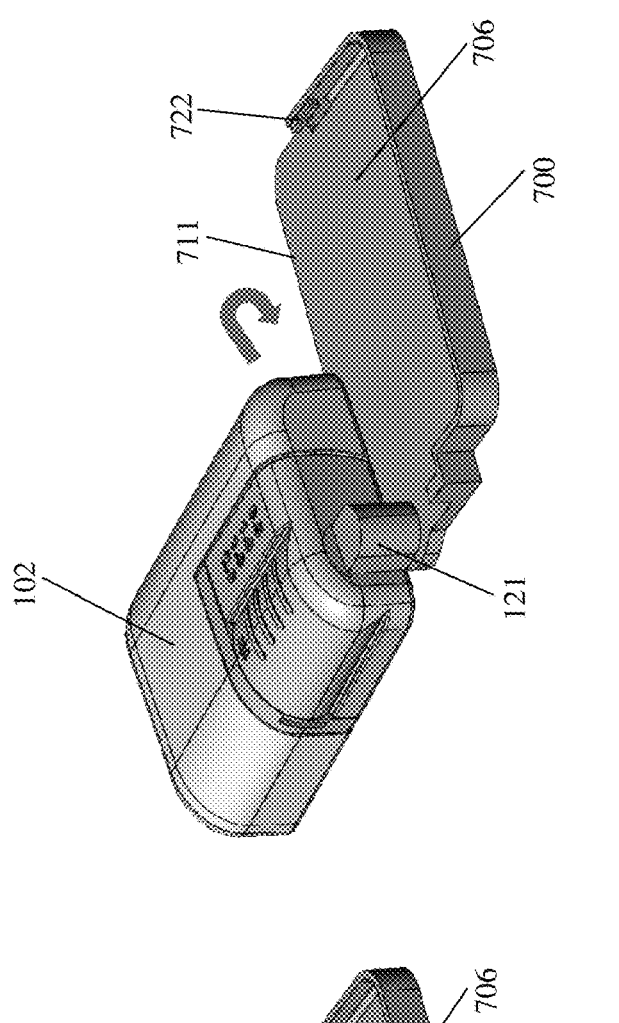
Figure 27C:
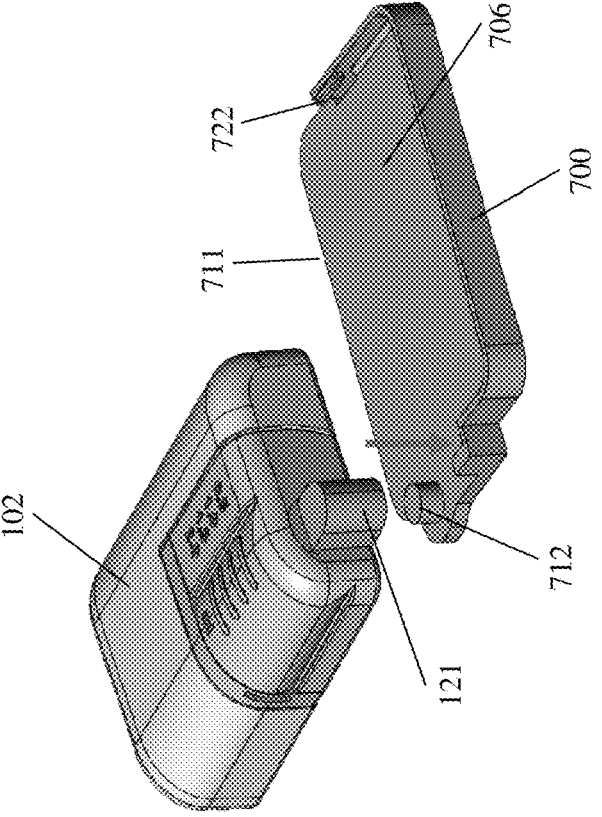
Figures 27E, 27F:
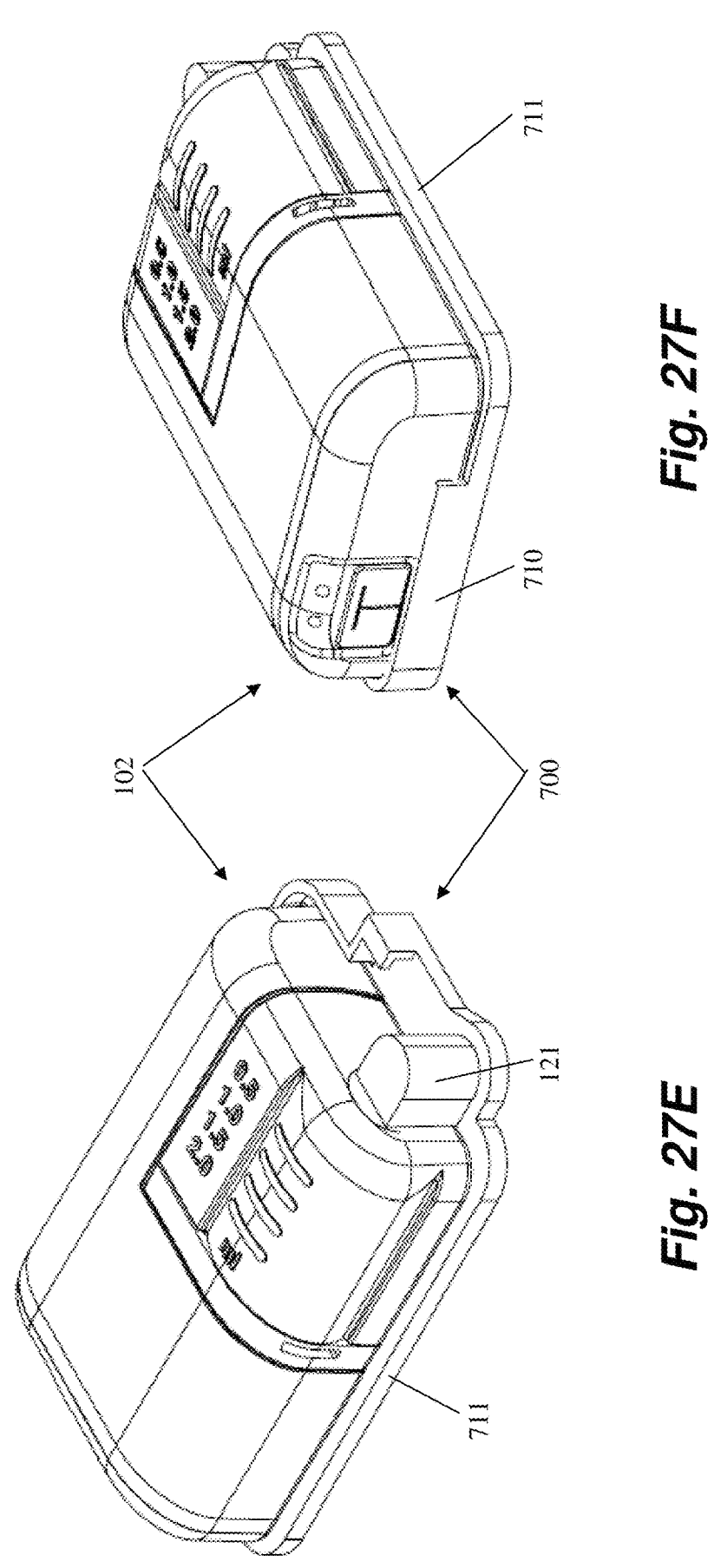

FIGS. 27A-27F depict an embodiment of a pump holder 700 for a pump system according to the disclosure. In this embodiment, the pump 102 attaches to the holder 700 via a rotational attachment. Cannula interface 121 of pump cartridge 116 can be inserted onto a cannula connector 712 in holder 700 with the pump 102 at an angle relative to holder 700 and then the pump 102 can be rotated about the cannula connector 712 to align the pump 102 on the holder 700. In one embodiment, as depicted in FIGS. 27C-27D, the pump 102 pump is rotated 90 degrees, but various other angles can be employed. Retention wall 710 of holder 700 can be a partial wall with an open portion 711 of base 706 enabling rotation of the pump 102 onto and into alignment with the base 706. Upon rotation of pump 102 into alignment with holder 700, one or more mating features can releasably hold the pump 102 on the holder 700. For example, a locking projection 722 extending from retention wall 710 of holder 700 can latch into a corresponding slot 164 in pump 102 to retain pump 102 on holder 700. The needle in cannula interface 121 is therefore vertically inserted through the cannula connector 712 upon initially connecting the pump 102 to the holder 700 and then rotates within cannula connector 712 as the pump 102 is rotated onto base 706. An adhesive patch can attach the holder 700 to a body of a user as with previous embodiments.

Figure 23:
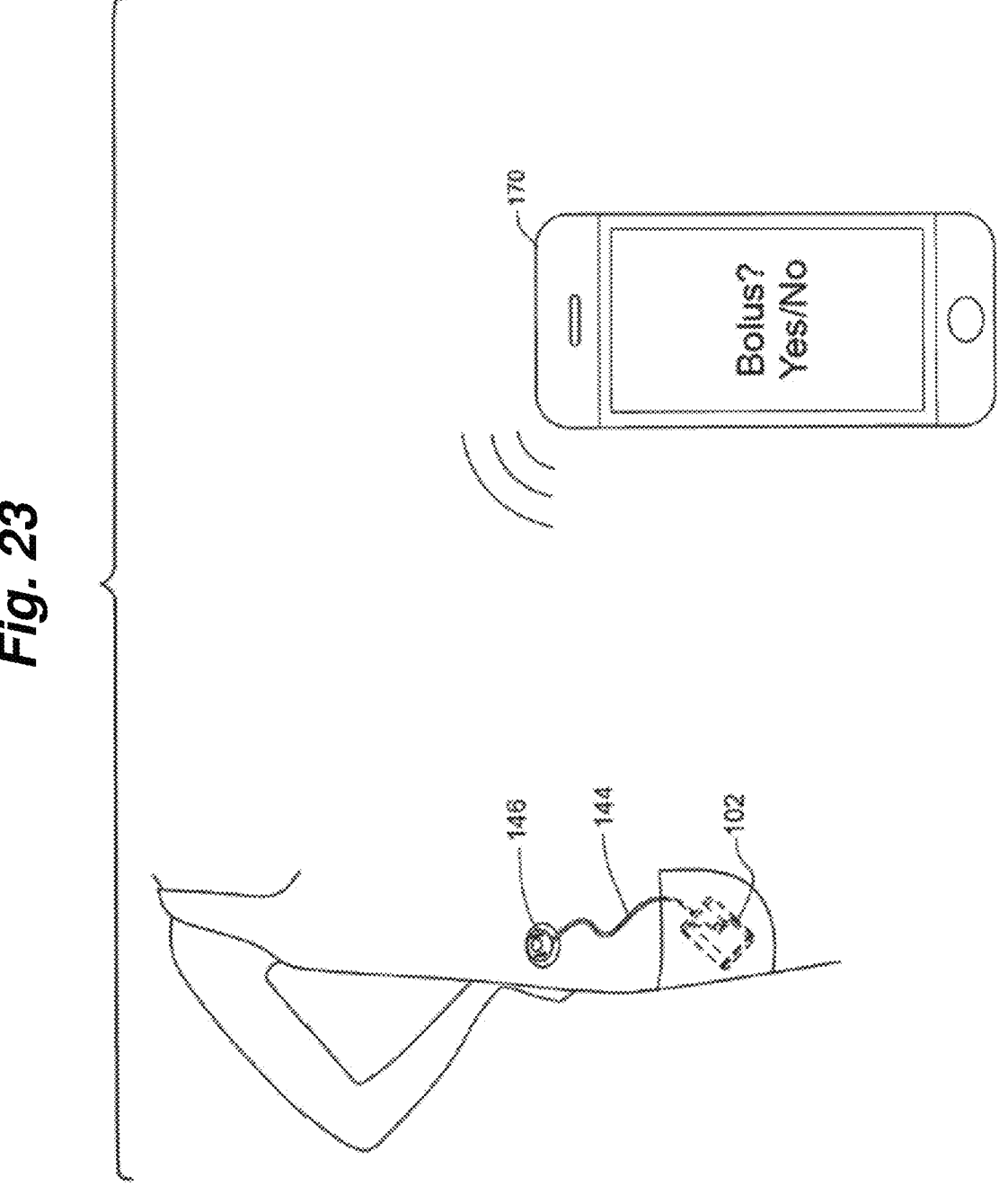
FIG. 23 depicts an embodiment of a pump system according to the disclosure.
Figure 24B:
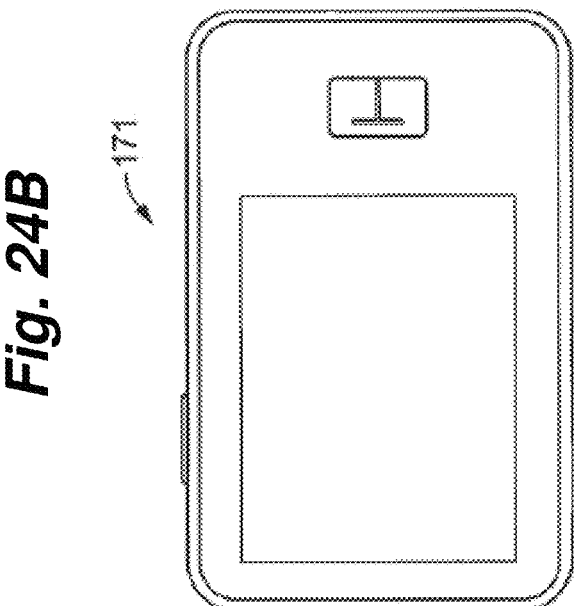
FIGS. 24A-24B depict remote control devices for a pump system according to embodiments of the disclosure.
Figure 24A:
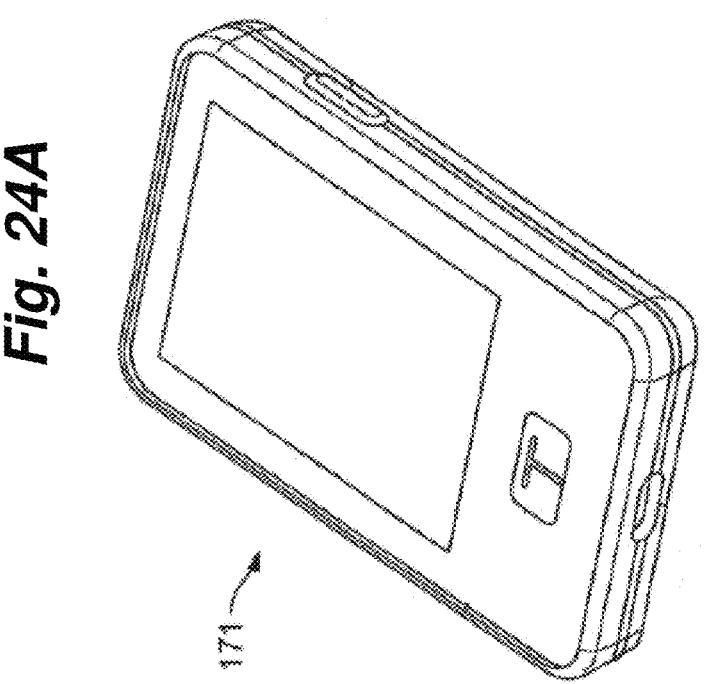

Referring to FIGS. 23-24B, one or more remote control devices 170, 171 can be used to communicate with the processor of pumps as disclosed herein to control delivery of medicament and transfer data with pump via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 23) executing a software application for control of the pump, a dedicated remote controller 171 (as depicted in FIGS. 24A-24B), a wearable electronic watch or electronic health or fitness monitor or personal digital assistant (PDA), etc., or a tablet, laptop or personal computer. Such communications between (and among) the one or more remote control devices 170, 171 and pump may be one-way or two-way for, e.g., effective transfer of data among the devices and the pump, control of pump operations, updating software on the devices and/or pump, and allowing pump-related data to be viewed on the devices and/or pump. Although pump 102 is shown in FIG. 23 as being carried by the user with an infusion set 144, 146 extending to the user's body, it should be understood that pumps worn directly on the body such as those described herein may also be controlled and communicate in such a manner.

Embodiments of the present invention include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

In an embodiment, a user-wearable infusion pump system can include a user-wearable infusion pump configured to contain a medicament including a flexible clip disposed on a perimeter of the user-wearable infusion pump and a pump holder configured to releasably hold the user-wearable infusion pump and including an adhesive patch configured to retain the pump holder on a body of a user. The pump holder comprising can include a frame base, a perimeter wall extending at least partially around the frame base having a shape matching the perimeter of the user-wearable infusion pump and a slot configured to selectively receive the flexible clip of the user-wearable infusion pump. The slot can provide a snap fit with the flexible clip to releasably retain the user-wearable infusion pump on the pump holder.

In some embodiments, the user-wearable infusion pump is configured to deliver the medicament to a user through a cannula extending through the pump holder directly below the user-wearable infusion pump.

In some embodiments, the user-wearable infusion pump comprises a drive unit and a cartridge selectively attachable to the drive unit and the flexible clip is disposed on the cartridge.

In some embodiments, the flexible clip comprises an elongate tab connected to the user-wearable infusion pump with a connector portion such that the elongate tab can flex inwardly and outwardly with respect to the user-wearable infusion pump via the connector portion.

In some embodiments, the flexible clip includes a locking projection having an upwardly facing locking surface configured to be seated within the slot of the pump holder to releasably retain the flexible clip in the slot.

In some embodiments, the slot is configured as a recess in the perimeter wall.

In some embodiments, the slot includes a downwardly facing surface configured to releasably retain the clip in the slot.

In some embodiments, the user-wearable infusion pump includes a retention slot formed in a body of the pump on an opposite end of the pump from the flexible clip and the pump holder includes a projection extending inwardly from the perimeter wall configured to interface with the retention slot of the pump.

In some embodiments, the user-wearable infusion pump includes a tab on an opposite end of the pump from the flexible clip and the pump holder includes a tab slot configured to interface with the tab on the pump.

In an embodiment, a pump holder for a user-wearable infusion pump can include an adhesive patch configured to retain the pump holder on a body of a user, a frame base and a perimeter wall extending at least partially around the frame base having a shape matching a perimeter of a user-wearable infusion pump. A slot can be configured to selectively receive a flexible clip of the user-wearable infusion pump to provide a snap fit with the flexible clip to releasably retain the user-wearable infusion pump on the pump holder.

In some embodiments, the slot is configured as a recess in the perimeter wall.

In some embodiments, the slot includes a downwardly facing surface configured to releasably retain the flexible clip in the slot.

In some embodiments, the pump holder includes a projection extending inwardly from the perimeter wall on a opposite end of the pump holder from the slot that is configured to interface with a retention slot of the user-wearable infusion pump.

In some embodiments, the pump holder includes a tab slot on a opposite end of the pump holder from the slot configured to interface with a tab on the pump.

In an embodiment, a user-wearable infusion configured to contain a medicament includes a flexible clip disposed on a perimeter of the user-wearable infusion pump. The flexible clip of the user-wearable infusion pump can be configured to provide a snap fit with a slot on a pump holder to releasably retain the user-wearable infusion pump on the pump holder.

In some embodiments, the user-wearable infusion pump comprises a drive unit and a cartridge selectively attachable to the drive unit, and the flexible clip is disposed on the cartridge.

In some embodiments, the flexible clip comprises an elongate tab connected to the user-wearable infusion pump with a connector portion such that the elongate tab can flex inwardly and outwardly with respect to the user-wearable infusion pump via the connector portion.

In some embodiments, the flexible clip includes a locking projection having an upwardly facing locking surface configured to be seated within the slot of the pump holder to releasably retain the flexible clip in the slot.

In some embodiments, the user-wearable infusion pump includes a retention slot formed in a body of the pump on an opposite end of the pump from the flexible clip configured to interface with a projection extending inwardly from a perimeter wall of the pump holder.

In some embodiments, the user-wearable infusion pump includes a tab on an opposite end of the pump from the flexible clip and the tab is configured to interface with a tab slot in the pump holder.

Although the embodiments herein have been specifically described with respect to a user-wearable infusion pump, the inventions disclosed herein could be employed with any other type of medical device capable of being worn on or near the body. Embodiments could further include non-medical applications, including smartphones. For example, a smartphone or other device could be placed into carriers such as those described herein to be interchangeably attached to various accessories.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; 10,569,016; 10,736,037; 10,888,655; 10,994,077; 11,116,901; 11,224,693; 11,291,763; 11,305,057; 11,458,246; and 11,464,908 and commonly owned U.S. Patent Publication Nos. 2009/0287180; 2012/0123230; 2013/0053816; 2014/0276423; 2014/0276569; 2014/0276570; 2018/0071454; 2019/0307952; 2020/0206420; 2020/0329433; 2020/0368430; 2020/0372995; 2021/0001044; 2021/0113766; 2021/0154405; 2021/0353857; 2022/0062553; 2022/0139522; 2022/0223250; 2022/0233772; 2022/0233773; 2022/0238201; 2022/0265927; and 2022/0344017 and commonly owned U.S. patent application Ser. Nos. 17/368,968; 17/732,208; 17/878,681; 17/879,959; 17/886,998; 17/896,492; 17/961,206; and Ser. No. 17/964,513.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A user-wearable infusion pump system, comprising:
a user-wearable infusion pump configured to contain a medicament, the user-wearable infusion pump including a movable clip disposed on a perimeter of the user-wearable infusion pump;
a pump holder configured to releasably hold the user-wearable infusion pump and including an adhesive patch configured to retain the pump holder on a body of a user, the pump holder comprising:
a frame base;
a perimeter wall extending at least partially around the frame base having a shape matching the perimeter of the user-wearable infusion pump; and
a slot configured to selectively receive a portion of the movable clip of the user-wearable infusion pump, the slot providing a snap fit with the movable clip to releasably retain the user-wearable infusion pump on the pump holder,
wherein the user-wearable infusion pump comprises a drive unit and a cartridge selectively attachable to the drive unit, and wherein the movable clip is disposed on the cartridge.

2. The user-wearable infusion pump system of claim 1, wherein the user-wearable infusion pump is configured to deliver the medicament to a user through a cannula extending through the pump holder directly below the user-wearable infusion pump.

3. The user-wearable infusion pump system of claim 1, wherein the movable clip comprises an elongate tab connected to the user-wearable infusion pump with a connector portion such that the elongate tab can flex inwardly and outwardly with respect to the user-wearable infusion pump via the connector portion.

4. The user-wearable infusion pump system of claim 1, wherein the movable clip includes a locking projection having a locking surface configured to be seated within the slot of the pump holder to releasably retain the movable clip in the slot.

5. The user-wearable infusion pump system of claim 1, wherein the slot is configured as a recess in the perimeter wall.

6. The user-wearable infusion pump system of claim 1, wherein the slot includes a surface configured to releasably retain the movable clip in the slot.

7. The user-wearable infusion pump system of claim 1, wherein the user-wearable infusion pump includes a retention slot formed in a body of the pump on an opposite end of the pump from the movable clip and the pump holder includes a projection extending inwardly from the perimeter wall configured to interface with the retention slot of the pump.

8. The user-wearable infusion pump system of claim 1, wherein the user-wearable infusion pump includes a tab on an opposite end of the pump from the movable clip and the pump holder includes a tab slot configured to interface with the tab on the pump.

9. A user-wearable infusion pump configured to contain a medicament, the user-wearable infusion pump comprising a movable clip disposed on a perimeter of the user-wearable infusion pump,
wherein the movable clip of the user-wearable infusion pump is configured to provide a snap fit with a slot on a pump holder to releasably retain the user-wearable infusion pump on the pump holder, wherein the user-wearable infusion pump comprises a drive unit and a cartridge selectively attachable to the drive unit, and wherein the movable clip is disposed on the cartridge.

10. The user-wearable infusion pump of claim 9, wherein the movable clip comprises an elongate tab connected to the user-wearable infusion pump with a connector portion such that the elongate tab can flex inwardly and outwardly with respect to the user-wearable infusion pump via the connector portion.

11. The user-wearable infusion pump of claim 9, wherein the movable clip includes a locking projection having a locking surface configured to be seated within the slot of the pump holder to releasably retain the movable clip in the slot.

12. The user-wearable infusion pump of claim 9, wherein the user-wearable infusion pump includes a retention slot formed in a body of the pump on an opposite end of the pump from the movable clip configured to interface with a projection extending inwardly from a perimeter wall of the pump holder.

13. The user-wearable infusion pump of claim 9, wherein the user-wearable infusion pump includes a tab on an opposite end of the pump from the movable clip and the tab is configured to interface with a tab slot in the pump holder.

\* \* \* \* \*